(12) United States Patent
Ponsati Obiols et al.

(10) Patent No.: US 12,297,294 B2
(45) Date of Patent: May 13, 2025

(54) CORTISTATIN ANALOGUES FOR THE TREATMENT OF INFLAMMATORY AND/OR IMMUNE DISEASES

(71) Applicant: BCN PEPTIDES, S.A., Saint Quinti de Mediona (ES)

(72) Inventors: Berta Ponsati Obiols, Barcelona (ES); Jimena Fernández Carneado, Villaviciosa (ES); Josep Farrera-Sinfreu, Tírvia (ES); Antonio Parente Dueña, Barcelona (ES)

(73) Assignee: BCN PEPTIDES, S.A., Sant Quinti de Mediona (ES)

(*) Notice: Subject to any disclaimer, the term of this patent is extended or adjusted under 35 U.S.C. 154(b) by 0 days.

(21) Appl. No.: 14/912,343

(22) PCT Filed: Sep. 17, 2014

(86) PCT No.: PCT/EP2014/069842
§ 371 (c)(1),
(2) Date: Feb. 16, 2016

(87) PCT Pub. No.: WO2015/040089
PCT Pub. Date: Mar. 26, 2015

(65) Prior Publication Data
US 2016/0185822 A1 Jun. 30, 2016

(30) Foreign Application Priority Data
Sep. 18, 2013 (EP) .................................... 13382361

(51) Int. Cl.
| A61K 38/10 | (2006.01) |
| A61K 45/06 | (2006.01) |
| C07K 7/08 | (2006.01) |
| C07K 14/575 | (2006.01) |
| C07K 14/655 | (2006.01) |

(52) U.S. Cl.
CPC ............. *C07K 7/08* (2013.01); *A61K 38/10* (2013.01); *A61K 45/06* (2013.01); *C07K 14/575* (2013.01); *C07K 14/655* (2013.01); *C07K 14/6555* (2013.01)

(58) Field of Classification Search
None
See application file for complete search history.

(56) References Cited

U.S. PATENT DOCUMENTS

| 7,074,761 B1 * | 7/2006 | Hinuma .............. C07K 14/575 514/11.1 |
| 8,435,940 B2 | 5/2013 | Bulaj et al. |
| 8,933,020 B2 | 1/2015 | Bulaj et al. |
| 8,946,154 B2 | 2/2015 | Dueña et al. |
| 2002/0142944 A1 | 10/2002 | Kuijpers et al. |
| 2009/0281031 A1 | 11/2009 | Bulaj et al. |
| 2011/0178013 A1 | 7/2011 | Paternostre et al. |
| 2012/0122781 A1 * | 5/2012 | Parente Duena .... C07K 14/655 514/11.1 |
| 2013/0244947 A1 | 9/2013 | Bulaj et al. |
| 2015/0203554 A1 | 7/2015 | Bulaj et al. |

FOREIGN PATENT DOCUMENTS

| EP | 1040837 A2 | 10/2000 |
| WO | WO-2007/081792 A2 | 7/2007 |
| WO | WO-2007/082980 A1 | 7/2007 |
| WO | WO-2009/043523 A2 | 4/2009 |
| WO | WO-2010/037930 A1 | 4/2010 |
| WO | WO-2010/128098 A1 | 11/2010 |

OTHER PUBLICATIONS

Gonzalez-Rey, Elena and Delgado, Mario; "Emergence of cortistatin as a new immunomodulatory factor with therapeutic potential in immune disorders." Mol. Cell. Endocrin. (2008) 286 p. 135-140.*
Broglio, Fabio et al, "Brain-gut communication: cortistatin, somatostatin, and ghrelin." Trends Endocrin. Metabol. (2007) 18(6) p. 246-251.*
Harris, A. G., "Somatostatin and somatostatin analogues: pharmacokinetics and pharmacodynamic effects." Gut (1994) sup 3 p. S1-S4.*
Holz, George G. and Chepurny, Oleg G., "Glucagon like peptide 1 synthetic analogs: new therapeutic agents for use in the treatment of diabetes millitus." Curr. Med. Chem. (2003) 10(22) p. 2471-2483.*
Pile, James C. and Longwirth, David L., "Should adults with suspected acute bacterial meningitis get adjunctive corticosterioids?" Cleveland Clin. J. Med. (2005) 72(1) p. 67-70.*
Table of IR peaks from https://webspectra.chem.ucla.edu/irtable.html, downloaded Jun. 25, 2024.*
Fawsett, . Ronald et al, "SOlvent induced frequency shifts in the infrared spectrum of acetonitrile in organic solvents." J. Phys. Chem. (1993) 97 p. 9293-9298.*
J. Fernandez-Carneado et al.; Fatty Acyl Moieties: Improving Pro-Rich Peptide Uptake Inside HeLa Cells; J.Peptide Res. 2005, vol. 65, No. 6.
International Search Report and Written Opinion of the ISA, ISA/EP, Rijswijk, NL, mailed Jan. 12, 2015.
Robas, Nicola, et al., "MrgX2 Is a High Potency Cortistatin Receptor Expressed in Dorsal Root Ganglion", The Journal of Biological Chemistry, 2003, pp. 44400-44404, vol. 278, No. 45, Issue of Nov. 7, The American Society for Biochemistry and Molecular Biology, Inc. (http://www.jbc.org).

(Continued)

*Primary Examiner* — Fred H Reynolds
(74) *Attorney, Agent, or Firm* — Harness, Dickey & Pierce, P.L.C.

(57) ABSTRACT

The invention relates to cortistatin analogues and their uses. The compounds of the invention are peptide ligands with potential application in the diagnosis, prevention or therapy of those pathologies where receptors capable of binding to cortistatin, specific or shared with other molecules such as somatostatin and/or ghrelin (GHSR), are expressed, being in addition more stable in serum than cortistatin.

7 Claims, No Drawings
Specification includes a Sequence Listing.

(56) References Cited

OTHER PUBLICATIONS

Albericio, Fernando, et al., "Preparation and Application of the 5-(4-(9-Fluorenylmethyloxycarbonyl) aminomethyl-3,5-dimethoxyphenoxy)-valeric Acid (PAL) Handle for the Solid-Phase Synthesis of C-Terminal Peptide Amides under Mild Conditions", 1990, pp. 3730-3743, vol. 55, No. 12, J. Org. Chem.

Atherton, E., et al., "Solid Phase Peptide Synthesis—a Practical Approach", The Practical Approach Series, 1989, pp. 1-16, IRL Press at Oxford University Press, Oxford, New York, Tokyo, p. 1-9, 16-21, and 47-61.

Barlos, Kleomenis, et al., "Darstellung Geschutzter Peptid-Fragmente Unter Einsatz Substituierter Triphenylmethyl-Harze", Tetrahedron Letters, pp. 3943-3946, vol. 30, No. 30, 1989, Maxwell Pergamon Macmillan plc, Great Britain. (In German).

Barlos, Kleomenis, et al., "Darstellung Geschutzter Peptid-Fragmente Unter Einsatz Substituierter Triphenylmethyl-Harze", Tetrahedron Letters, pp. 3947-3950, vol. 30, No. 30, 1989, Maxwell Pergamon Macmillan plc, Great Britain. (In German).

Berge, Stephen M., et al., "Pharmaceutical Salts", Journal of Pharmaceutical Sciences, Jan. 1977, pp. 1-19, vol. 66, No. 1.

Bevan, John S., "Clinical Review: The Antitumoral Effects of Somatostatin Analog Therapy in Acromegaly", The Journal of Clinical Endocrinolgy & Metabolism, pp. 1856-1863, The Endocrine Society (http://www.endo-society.org), 2005.

Bodanszky, M., et al., "The Practice of Peptide Synthesis", 2nd Edition, 1984, Springer Lab Manual, Springer-Verlag, Berlin, Heidelberg, New York, London, Paris, Tokyo, Hong Kong, Barcelona, Budapest.

Martin-Gago, Pablo, et al., "Fine-tuning the p-p Aromatic Interactions in Peptides: Somatostatin Analogues Containing Mesityl Alanine", Angewandte Communications, Angew. Chem. Int. Ed. 2012, pp. 1820-1825, vol. 51, Wiley-VCH Verlag Gmbh & Co. KGaA, Weinheim.

Dalm, Virgil A.S.H., et al., "Expression of Somatostatin, Cortistatin, and Somatostatin Receptors in Human Monocytes, Macrophages, and Dendritic Cells", Am J. Physiol Endocrinol Metab (http://www.ajpendo.org), 2003, pp. E344-E353, vol. 285, The American Physiological Society.

Dalm, Virgil A., "Cortistatin Rather Than Somatostatin as a Potential Endogenous Ligand for Somatostatin Receptors in the Human Immune System", The Journal of Clinical Endocrinology & Metabolism, 2003, pp. 270-276, The Endocrine Society.

De Lecea, Luis, et al., "A Cortical Neuropeptide With Neuronal Depressant and Sleep-Modulating Properties", Letters to Nature, May 16, 1996, pp. 242-245, vol. 381, Departments of Molecular Biology and Neuropharmacology, The Scripps Research Institute, USA.

Fukusumi, Shoji, et al., "Identification and Characterization of a Novel Human Cortistatin-like Peptide", Biochemical Biophysical Research Communications, 1997, pp. 157-163, vol. 232, Article No. RC976252, Academic Press.

Gonzalez-Rey, Elena, "Cortistatin, a New Antiinflammatory Peptide with Therapeutic Effect on Lethal Endotoxemia", Institute of Parasitology and Biomedicine, 2006, pp. 563-571, vol. 203, No. 3, The Journal of Experimental Medicine (jem.rupress.org), The Rockefeller University Press.

Gonzalez-Rey, Elena, et al., "Cortistatin, an Antiinflammatory Peptide with Therapeutic Action in Inflammatory Bowel Disease", PNAS (www.pnas.org), pp. 4228-4233, vol. 103, No. 11, 2006.

Gonzalez-Ray, Elena, et al., "Therapeutic Effect of Cortistatin on Experimental Arthritis by Downregulating Inflammatory and Th1 Responses", Extended Report, Ann Rheum Dis, 2006, pp. 582-588.

Gonzalez-Rey, Elena, et al., "Emergence of Cortistatin as a New Immunomodulatory Factor with Therapeutic Potential in Immune Disorders", Molecular and Cellular Endocrinology (www.elsevier.com), 2008, pp. 135-140, vol. 286.

Greene, Theodora W., et al., "Protective Groups in Organic Synthesis", John Wiley & Sons, Inc., 1999, A Wiley-Interscience Publication, Third Edition, USA and Canada, chapter 1 only.

IUPAC-IUB Joint Commission on Biochemical Nomenclature, "Nomenclature and Symbolism for Amino Acids and Peptides", Eur. J. Biochem., 1984, pp. 9-37, vol. 138, FEBS.

Kullmann, Willi, "Proteases as Catalysts for Enzymic Syntheses of Opioid Peptides", The Journal of Biological Chemistry, 1980, pp. 8234-8238, vol. 255, No. 17.

Lloyd-Williams, Paul, et al., "Convergent Solid-Phase Peptide Synthesis", Tetrahedron Report Number 347, 1993, pp. 11065-11133, vol. 49, No. 48.

Lloyd-Williams, Paul, et al., "Chemical Approaches to the Synthesis of Peptides and Proteins", 1997, pp. 19-93, CRC Press.

Smith, Michael B., et al., "March's Advanced Organic Chemistry—Reactions, Mechanisms, and Structure", 2001, a Wiley-Interscience Publication, John Wiley & Sons, Inc, p. 557, 597, 389-445, 448-599.

Matsueda, Gary R., et al., "A p-Methylbenzhydrylamine Resin for Improved Solid-Phase Synthesis of Peptides Amides", Peptides, 1981, pp. 45-50, vol. 2, ANKHO International Inc.

Meyers, Chester A., et al., "Use of the Mouse Vas deferens Assay to Evaluate the Action of Somatostatin Peptides on Gastric Acid Secretion", Digestion, 1981, pp. 21-24, Tulane University School of Medicine.

Patel, Yogesh C., et al., "Subtype Selectivity of Peptide Analogs for All Five Cloned Human Somatostatin Receptors", Endocrinology, 1994, pp. 2814-2817, vol. 135, No. 6, The Endocrine Society (endo.endojournals.org).

Rink, Hans, "Solid-Phase Synthesis of Protected Peptide Fragments Using a Trialkoxy-Diphenyl-Methylester Resin", Tetrahedron Letters, 1987, pp. 3787-3790, vol. 28, No. 33, Pergamon Journals Ltd.

Rowe, Raymond C., et al., "Handbook of Pharmaceutical Excipients", Sixth Edition, 2009, Pharmaceutical Press and American Pharmacists Association.

Skamene, A. et al., "Infusion of Graded Concentrations of Somatostatin in Man: Pharmacokinetics and Somatostatin in Man: Pharmacokinetics and Differential Inhibitory Effects on Pituitary and Islet Hormones", Clinical Endocrinology, 1984, pp. 554-564.

Spier, Avron D., et al., "Cortistatin: A Member of the Somatostatin Neuropeptide Family with Distinct Physiological Functions", Brain Research Reviews, 2000, pp. 228-241, vol. 33, Elsevier Science B.V.

Stewart, John Morrow, et al., "Solid Phase Peptide Synthesis", Second Edition, 1984, pp. 1-9 and 70-95, Pierce Chemical Company.

Van Hagen, P. Martin, et al., "The Role of Cortistatin in the Human Immune System", Molecular and Cellular Endocrinology, 2008, pp. 141-147, vol. 286, Elsevier Ireland Ltd. (www.elsevier.com/locate/mce).

Wang, Su-Sun, "p-Alkoxybensyl Alcohol Resin and p-Alkoxybensyloxycarbonylhydrazide Resin for Solid Phase Synthesis of Protected Peptide Fragments", Chemical Research Department, Hoffman-La Roche Inc., 1973, pp. 1328-1333, vol. 95, No. 4, Journal of the American Chemical Society.

Chicharro, Cristina et al., "N-Terminal Fatty Acid Substitution Increases the Leishmanicidal Activity of CA(1-7)M(2-9), a Cecropin-Melittin Hybrid Peptide." Antimicrobial Agents and Chemotherapy, vol. 45, No. 9, pp. 2441-2449 (2001).

Hirst, Barry H. et al., "Structure-activity studies with somatostatin: role of lysine in positions 4 and 9 for gastric activity." Regulatory Peptides, vol. 8, No. 4, pp. 267-271 (1984).

Rosenthal, Linda E. et al., "Structure-Activity Relationships of Somatostatin Analogs in the Rabbit Ileum and the Rat Colon." Journal of Clinical Investigation, vol. 71, No. 4, pp. 840-849 (Apr. 1983).

UniProt Consortium, "UniProtKB—000230 (Cort_Human)." www.uniprot.org/uniprot/O00230#PRO_0000033156, last modified Oct. 7, 2020.

Adessi, Celine et al., "Converting a Peptide into a Drug: Strategies to Improve Stability and Bioavailability." Current Medicinal Chemistry, vol. 9, No. 9, pp. 963-978 (2002).

Córdoba-Chacón, José et al., "Cortistatin Is Not a Somatostatin Analogue but Stimulates Prolactin Release and Inhibits GH and ACTH in a Gender-Dependent Fashion: Potential Role of Ghrelin." Endocrinology, vol. 152, No. 12, pp. 4800-4812 (Dec. 2011).

(56) References Cited

OTHER PUBLICATIONS

Hirst, B.H. et al., "Structure-activity studies with somatostatin: The role of tryptophan in position 8." Regulatory Peptides, vol. 1, No. 2, pp. 97-113 (Oct. 1980).
Bowie, James et al., "Deciphering the Message in Protein Sequences: Tolerance to Amino Acid Substitutions", Science, Mar. 16, 1990; 47, 4948; ProQuest, pp. 1306-1310.
Rol, Alvaro et al., "Structure-based design of a Cortistatin analogue with immunomodulatory activity in models of inflammatory bowel disease", Nature Communications, https://doi.org/10.1038/s41467-021-22076-5, pp. 1-15, Published online: Mar. 25, 2021.

* cited by examiner

CORTISTATIN ANALOGUES FOR THE TREATMENT OF INFLAMMATORY AND/OR IMMUNE DISEASES

CROSS-REFERENCE TO RELATED APPLICATIONS

This application is a 371 U.S. National Stage of International Application No. PCT/EP2014/069842, filed Sep. 17, 2014, which claims the benefit of and priority to European Patent Application No. 13382361.7, filed Sep. 18, 2013. The entire disclosures of the above applications are incorporated herein by reference.

FIELD OF INVENTION

The invention relates to cortistatin analogues and their uses. The compounds of the invention are peptide ligands with potential application in the diagnosis, prevention or therapy of those pathologies where receptors capable of binding to cortistatin are expressed.

BACKGROUND OF INVENTION

Cortistatin (CST) is a natural endogenous peptide of 14 amino acids, discovered in rats in 1996 (CST-14) [de Lecea et al., Nature, 1996, 381, 242-245] and later in 1997, found in humans as an extended form of 17 amino acids (CST-17) [Fukusimi et al., Biochem. Biophys. Res. Commun, 1997, 232, 157-163]. Cortistatin, in fact, exists in two biologically active forms as its precursor (prepro-CST) gives rise to CST-14 and CST-29 in rodents and to CST-17 and CST-29 in humans.

Cortistatin has a high homology to another endogenous peptide, somatostatin (SST), which is highly conserved and found in mammals in the form of somatostatin-14 (SST-14) and somatostatin-28 (SST-28):

Sequences of cortistatin and somatostatin

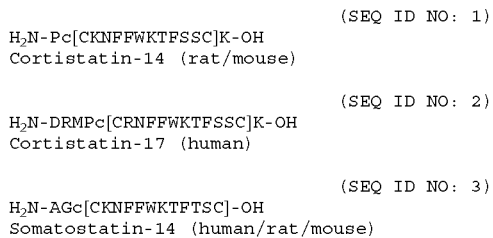

In fact, cortistatin interacts with the 5 G protein-coupled membrane receptors described for somatostatin, sstr1-sstr5 [a) Spier et al., Brain Research Reviews 2000, 33, 228-241; b) Patel et al., Endocrinology 1994, 135, 2814-2817]. But cortistatin is not somatostatin [Gonzalez-Rey et al., Mol. Cell. Endocrinol. 2008, 286 (1-2), 135-140], and thus, in addition to its nanomolar affinity to somatostatin receptors, cortistatin also interacts with the Ghrelin receptor (GHSR). Furthermore, in the search for a specific receptor for cortistatin, the orphan receptor MrgX2 was described as the first human specific receptor for cortistatin [Robas et al., J. Biol. Chem. 2003, 278, 44400-44404]. Subsequently, the absence of this receptor in cells of the immune system and its high affinity for other neuropeptides, such as proadrenomedullin, have made that nowadays it is not considered as a specific cortistatin receptor [van Hagen et al., Mol. Cell. Endocrinol. 2008, 286 (1-2), 141-147] and characterisation of a specific cortistatin receptor is an issue that remains unresolved.

Cortistatin's immunomodulatory activity has been widely demonstrated in experimental models of diseases that course with inflammatory and autoimmune responses such as Lethal Endotoxin Shock, Crohn's Disease and Rheumatoid arthritis [a) Gonzalez-Rey et al., J. Exp. Med. 2006, 203(3), 563-571; b) Gonzalez-Rey et al., Proc. Natl. Acad. Sci. USA 2006, 103, 4228-4233; c) Gonzalez-Rey et al., Ann. Rheum. Dis. 2007, 66 (5), 582-588; d) WO 2007/082980 A1]. Said immunoregulatory action may be correlated with its expression in lymphocytes, monocytes, macrophages and dendritic cells and cells of the immune system [a) Dalm V. A. et al., Am. J. Physiol. Endocrinol. Metab. 2003, 285, E344-353; b) Dalm V. A. et al., J. Clin. Endocrinol. Metab. 2003, 88, 270-276]. The expression of cortistatin and its receptors in the human immune system and pathologies of the immune system has recently been reviewed [van Hagen et al., Mol. Cell. Endocrinol. 2008, 286 (1-2), 141-147].

In the above referenced research studies that showed cortistatin's efficacy in diseases with inflammatory and immune component, CST-29 was used. CST-29 is a long endogenous peptide, of high synthetic difficulty and therefore low industrial viability for its industrial application in the pharmaceutical sector. Its pharmaceutical use also presents an additional problem: its low serum stability.

Other proposals under study prove the efficacy of the endogenous peptide CST-17 combined with the neuropeptide El for the treatment of inflammatory and autoimmune diseases [WO 2009/043523 A2], which presents the advantage of a lower synthetic difficulty for its industrial use. However, it still possesses the disadvantage of having a low stability in serum due to its native structure with L-amino acids.

Generally, peptide-based drugs are advantageous because peptides are intrinsically non-toxic, their efficacy at low doses ensures that they do not cause significant side effects in comparison to other drugs based on small molecules or on antibodies, but they do have to be modified to improve their bioavailability and half-life. The incorporation of non-natural amino acids into the natural sequence is one of the strategies known in prior art for increasing an endogenous peptide's stability. For example, modifications of somatostatin with halogenated amino acids, with p-chloro-Phe and pentafluoro-Phe in positions 6, 7 and 11 have been described [WO 2007/081792 A2; Meyers C. A. et al., Digestion 1981, 21(1), 21-4]. The same positions 6, 7 and 11 of original somatostatin have also been modified with mesitylalanine and mesitylglycine, resulting in somatostatin analogues that are more stable [WO 2010/128098 A1]. However these stabilizing modifications may compromise the functionality of the original molecule. This is the case of octreotide, a somatostatin analogue in clinical use that is much more stable than the original molecule, which keeps binding to the sstr2 receptor but completely loses its affinity to the sstr1 and sstr4 receptors. [Patel et al., Endocrinology 1994, 135, 2814-2817].

The blood half-life of endogenous peptides such as somatostatin and cortistatin is extremely short, barely reaching a few minutes [Skamene et al., Clin. Endocrinol. 1984, 20, 555-564]. Thus, there is a need to find new synthetic cortistatin analogues for the treatment of those pathologies in which specific cortistatin receptors and those receptors shared with other molecules like somatostatin (sstr1, sstr2, sstr3, sstr4 and/or sstr5) and/or ghrelin (GHSR) are expressed, being, furthermore, more stable in blood than cortistatin.

DETAILED DESCRIPTION OF THE INVENTION

This invention discloses new peptides, cortistatin analogues, with anti-inflammatory and/or immunoregulatory action, similar to that of the natural peptide. Certain modifications with non-natural amino acids, such as mesitylalanine and/or dihalogenophenylalanines, plus the incorporation of fatty acids or PEGylations, preserve and even improve the anti-inflammatory and anti-autoimmune action of the natural molecule in vitro and in vivo. In addition, the main benefit of the new cortistatin analogues is that the resulting peptides, with one or several modifications, possess a substantially longer half-life in serum than that of the endogenous molecule. The synthesis of the new cortistatin analogues is economically viable (with sequences of preferably 13 to 17 amino acids), an aspect which guarantees their usefulness in the pharmaceutical industry. The compounds of this invention are new compounds and are functionally equivalent to cortistatin as they all feature an anti-inflammatory and/or immunoregulatory effect similar to cortistatin in vitro and/or in vivo.

Definitions

Herein included are the meanings of some terms and expressions as they are employed in the context of the invention, with the aim of aiding its comprehension.

The term "cortistatin analogue" refers to a compound that interacts with at least one of the cortistatin receptors known and shared with other molecules, such as the 5 somatostatin receptors (sstr1, sstr2, sstr3, sstr4 and/or sstr5) or the ghrelin receptor and/or a specific cortistatin receptor still to be identified. It is therefore a ligand of said cortistatin receptors and may be functionally equivalent (or an agonist) of cortistatin, with an activity similar to that of cortistatin.

The term "functionally equivalent (or agonist)" refers to a compound that shows affinity for some of the original molecule's receptors and, from a qualitative point of view, produces the same effects as the endogenous ligand of the receptor.

The term "somatostatin analogue" refers to a compound that interacts with one or more somatostatin receptors (sstr) and is also known as a ligand of said receptors. This definition was introduced by Bevan et al. [in *J. Clin. Endocrinol. Metabolism.* 2005, 90, 1856-1863]. In EP 1040837 A2 the term somatostatin analogue is also defined in reference to all the modified derivatives of native somatostatin that show a somatostatin related activity, such as interacting with at least one of the somatostatin receptors (sstr1, sstr2, sstr3, sstr4 or sstr5)".

In this description, the abbreviations used for amino acids comply with the rules of the IUPAC-IUB Biochemical Nomenclature Committee laid out in *Eur. J. Biochem,* 1984, 138, 9-37 (FIG. 1).

FIG. 1: Amino acids (stereochemistry not specified, in all cases it may be L-, D- or DL-)

Ala (A): Alanine
Asn (N): Asparagine
Asp (D): Aspartic acid
Arg (R): Arginine
Cys (C): Cysteine
Gly (G): Glycine
Lys (K): Lysine
Met (M): Methionine
Phe (F): Phenylalanine
Pro (P): Proline
Ser (S): Serine
Thr (T): Threonine
Trp (W): Tryptophan
Phg: Phenylglycine

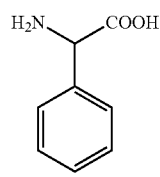

Msa: 2,4,6-trimethylphenylalanine or 3-mesitylalanine

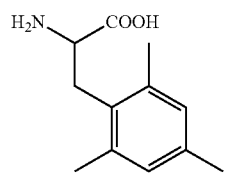

Tmp: 3,4,5-trimethylphenylalanine

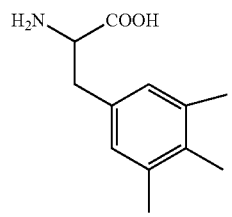

Msg: 2,4,6-Trimethylphenylglycine or 2-mesitylglycine

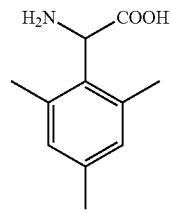

3,4,5-Trimethylphenylglycine

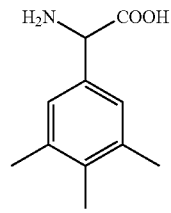

DiW-Phe (where W is F, Cl, Br or I): Dihalogenophenylalanine, which is a phenylalanine where the phenyl group is substituted with two halogen atoms.

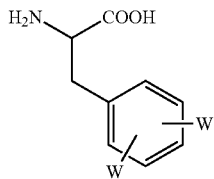

Dfp: 3,5-Difluorophenylalanine

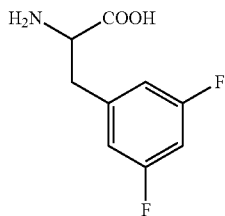 [SMILES: NC(Cc1cc(F)cc(F)c1)C(=O)O]

The abbreviation "Ac-" is used in this description to identify the acetyl group ($CH_3$—CO—), the abbreviation "Palm-" is used to identify the palmitoyl group ($CH_3$—$(CH_2)_{14}$—CO—) and the abbreviation "Myr-" is used to identify the myristoyl group ($CH_3$—$(CH_2)_{12}$—CO—).

The term "non-cyclic aliphatic group" is used in this invention to cover the linear or branched alkyl, alkenyl and alkynyl groups.

The term "alkyl group" refers to a saturated, linear or branched group, which has between 1 and 24, preferably between 1 and 16, more preferably between 1 and 14, even more preferably between 1 and 12, yet more preferably 1, 2, 3, 4, 5, 6, 7 or 8 carbon atoms and that is bound to the rest of the molecule by a single bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and such like.

The term "alkenyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more carbon-carbon double bonds, preferably with 1, 2 or 3 carbon-carbon double bonds, conjugated or unconjugated, which is bound to the rest of the molecule by a single bond, including, for example and not restricted to, the vinyl (—$CH_2$=$CH_2$), allyl (—$CH_2$—CH=$CH_2$), oleyl, linoleyl groups and such like.

The term "alkynyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more carbon-carbon triple bonds, preferably 1, 2 or 3 carbon-carbon triple bonds, conjugated or unconjugated, which is bound to the rest of the molecule by a single bond, including, for example and not restricted to, the ethynyl group, 1-propinyl, 2-propinyl, 1-butinyl, 2-butinyl, 3-butinyl, pentinyl, such as 1-pentinyl and such like. The alkynyl groups can also contain one or more carbon-carbon double bonds, including, for example and not restricted to, the but-1-en-3-inyl, pent-4-en-1-inyl groups and such like.

The term "alicyclic group" is used in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably 3, 4, 5 or 6 carbon atoms and which is bound to the rest of the molecule by a single bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and such like.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more carbon-carbon double bonds, preferably 1, 2 or 3 carbon-carbon double bonds, conjugated or unconjugated, which is bound to the rest of the molecule by a single bond, including, for example and not restricted to, the cyclopent-1-en-1-yl group and such like.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more carbon-carbon triple bonds, preferably 1, 2 or 3 carbon-carbon triple bonds, conjugated or unconjugated, which is bound to the rest of the molecule by a single bond, including, for example and not restricted to, the cyclooct-2-in-1-yl group and such like. Cycloalkynyl groups can also contain one or more carbon-carbon double bonds, including, for example and not restricted to, the cyclooct-4-en-2-inyl group and such like.

The term "aryl group" refers to an aromatic group which has between 6 and 30, preferably between 6 and 18, more preferably between 6 and 10, yet more preferably 6 or 10 carbon atoms, which comprises 1, 2, 3 or 4 aromatic rings, bound by a carbon-carbon bond or which are condensed, including, for example and not restricted to, phenyl, naphthyl, diphenyl, indenyl, phenanthryl oranthranyl, among others; or to an aralkyl group.

The term "aralkyl group" refers to an alkyl group substituted by an aromatic group, with between 7 and 24 carbon atoms and including, for example and not restricted to, —$(CH_2)_{1-6}$-phenyl, —$(CH_2)_{1-6}$-(1-naphthyl), —$(CH_2)_{1-6}$-(2-naphthyl), —$(CH_2)_{1-6}$—CH(phenyl)$_2$ and such like.

The term "heterocyclyl group" refers to a hydrocarbonated ring of 3-10 members, in which one or more of the atoms in the ring, preferably 1, 2 or 3 of the atoms in the ring, is an element different to carbon, such as nitrogen, oxygen or sulfur and can be saturated or unsaturated. For the purposes of this invention, the heterocycle can be a cyclic, monocyclic, bicyclic or tricyclic system, which may include systems of condensed rings; and the nitrogen, carbon or sulfur atoms in the heterocyclyl radical may be optionally oxidized; the nitrogen atom may be optionally quaternized; and the heterocyclyl radical may be partially or completely saturated or be aromatic. The greatest preference is for the term heterocyclyl to refer to a ring of 5 or 6 members. Examples of saturated heterocyclyl groups are dioxane, piperidine, piperazine, pyrrolidine, morpholine and thiomorpholine. Examples of aromatic heterocyclyl groups, also known as heteroaromatic groups are pyridine, pyrrole, furan, thiophene, benzofuran, imidazoline, quinolin, quinoline, pyridazine and naphthyridine.

The term "heteroarylalkyl group" refers to an alkyl group substituted by a substituted or unsubstituted aromatic heterocyclyl group, the alkyl group having from 1 to 6 carbon atoms and the aromatic heterocyclyl group between 2 and 24 carbon atoms and from 1 to 3 atoms different to carbon including, for example and not restricted to, —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and such like.

As is understood in this technical field, there may be a certain degree of substitution in the groups defined above. Therefore, there may be substitution in the groups of this invention where it is explicitly indicated so. The references in this document to substituted groups in the groups of this invention indicate that the specified radical can be substituted in one or more positions available by one or more substituents, preferably in 1, 2 or 3 positions, more preferably in 1 or 2 positions, yet more preferably in 1 position. These substituents include, for example and not restricted to, alkyl $C_1$-$C_4$; hydroxyl; alcoxyl $C_1$-$C_4$; amino; aminoalkyl $C_1$-$C_4$; carbonyloxyl $C_1$-$C_4$; oxycarbonyl $C_1$-$C_4$; halogen such as fluorine, chlorine, bromine and iodine; cyano; nitro; azide; alkylsulfonyl $C_1$-$C_4$; thiol; alkylthio $C_1$-$C_4$; aryloxyl such as phenoxyl; —$NR_b(C=NR_b)NR_bR_c$; wherein Rb and $R_c$ are independently selected from the group consisting of H, alkyl $C_1$-$C_4$, alkenyl $C_2$-$C_4$, alkynyl $C_2$-$C_4$, cycloalkyl $C_3$-$C_{10}$, aryl $C_6$-$C_{18}$, aralkyl $C_7$-$C_{17}$, heterocyclyl of 3-10 members or protective group of the amino group.

Compounds in the Invention

A first aspect of this invention refers to a compound defined by formula (I),

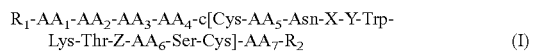

its stereoisomers, mixtures thereof and/or its pharmaceutically acceptable salts, wherein $AA_1$ is Asp or a bond
$AA_2$ is Arg or a bond
$AA_3$ is Met or Ala or a bond
$AA_4$ is Pro or Gly
$AA_5$ is Lys or Arg
$AA_6$ is Ser or Thr
$AA_7$ is Lys or a bond
X, Y, Z are the amino acids Phe, Phg, Msa, 3,4,5-trimethylphenylalanine, Msg, 3,4,5-trimethylphenylglycine and/or a dihalogenophenylalanine, diW-Phe;
W is selected from the group consisting of F, Cl, Br and I;
$R_1$ is selected from the group consisting of H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl, a polymer derived from polyethylene glycol, a chelating agent and $R_5$—CO—;
$R_2$ is selected from the group consisting of —$NR_3R_4$, —$OR_3$ and —$SR_3$;
$R_3$ and $R_4$ are independently selected from the group consisting of H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl and a polymer;
$R_5$ is selected from the group consisting of H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

and with the condition that:
At least one of the amino acids X, Y or Z is Msa, 3,4,5-trimethylphenylalanine, Msg, 3,4,5-trimethylphenylglycine and/or a dihalogenophenylalanine, diW-Phe;
If $AA_1$ and $AA_2$ are bonds, $AA_3$ is Ala, $AA_4$ is Gly, $AA_5$ is Lys, $AA_6$ is Thr and $AA_7$ is a bond, then at least one of the amino acids X, Y or Z is a dihalogenophenylalanine, diW-Phe.

In a preferred embodiment, at least one of the amino acids X, Y or Z is a dihalogenophenylalanine, diW-Phe. Preferably, W is fluorine. More preferably the dihalogenophenylalanine is 3,5-difluorophenylalanine (Dfp).

In a preferred embodiment, $AA_4$ is Pro. In a more preferable embodiment, $AA_3$ is Met or a bond and $AA_4$ is Pro. Preferably, at least one of the amino acids X, Y or Z is Msa and/or 3,5-difluorophenylalanine (Dfp).

The $R_1$ and $R_2$ groups are bound to the amino-terminal (N-terminal) and carboxy-terminal (C-terminal) ends of the peptide sequences respectively, and they may be amino acids.

In accordance with a preferred embodiment of this invention, $R_1$ is selected from the group consisting of H, a polymer derived from polyethylene glycol and $R_5$—CO—, wherein $R_5$ is selected from the group consisting of substituted or unsubstituted alkyl radical $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon where the alkyl chain is of 1 to 6 carbon atoms. More preferably, $R_1$ is selected from the group consisting of H, acetyl, tert-butanoyl, prenyl, hexanoyl, 2-methylhexanoyl, cyclohexanecarboxyl, octanoyl, decanoyl, lauroyl, myristoyl, palmitoyl, stearoyl, behenyl, oleoyl and linoleoyl. Even more preferably, $R_1$ is H, acetyl, hexanoyl, octanoyl, lauroyl, myristoyl or palmitoyl.

In accordance with another preferred embodiment, $R_1$ is selected from a polymer derived from polyethylene glycol with a molecular weight comprised between 200 and 35000 Daltons.

In accordance with another preferred embodiment, $R_2$ is —$NR_3R_4$, —$OR_3$ or —$SR_3$, wherein $R_3$ and $R_4$ are independently selected from the group consisting of H, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon, wherein the alkyl chain is of 1 to 6 carbon atoms and a polymer derived from polyethylene glycol. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$, where $R_3$ and $R_4$ are independently selected from the group consisting of H, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{10}$, substituted or unsubstituted aryl $C_6$-$C_{15}$, substituted or unsubstituted heteroarylalkyl ring of 3 to members and an alkyl chain of 1 to 6 carbon atoms and a polymer derived from polyethylene glycol. More preferably $R_3$ and $R_4$ are selected from the group consisting of H, methyl, ethyl, hexyl, dodecyl or hexadecyl. Even more preferably $R_3$ is H and $R_4$ is selected from the group consisting of H, methyl, ethyl, hexyl, dodecyl or hexadecyl. In accordance with an even more preferred embodiment, $R_2$ is selected from —OH and —$NH_2$.

In accordance with a preferred embodiment of this invention, $R_1$ or $R_2$ is a chelating agent that is optionally complexed, with a detectable or radio-therapeutic element. A chelating agent refers to a group that is capable of forming coordination complexes with the detectable or radiotherapeutic element. Preferably, the chelating agent is a group capable of forming complexes with metal ions, more preferably selected from the group consisting of DOTA, DTPA, TETA or derivatives thereof. The chelating agent can be bound directly or via a linker.

Detectable element refers to any radioactive, fluorescent or positive contrast magnetic resonance imaging element, preferably a metal ion, which shows a detectable property in an in vivo diagnostic technique. Radiotherapeutic element is understood as any element which emits α-radiation, β-radiation, or γ-radiation.

In a specific embodiment, the compounds of the invention are selected from the group of sequences described below:

(SEQ ID NO: 4)
Ala-Gly-c[-Cys-Lys-Asn-Phe-Dfp-Trp-Lys-Thr-Phe-
Thr-Ser-Cys]

(SEQ ID NO: 5)
Ala-Gly-c[Cys-Lys-Asn-Dfp-Phe-Trp-Lys-Thr-Phe-
Thr-Ser-Cys]

(SEQ ID NO: 6)
Ala-Gly-c[Cys-Lys-Asn-Phe-Phe-Trp-Lys-Thr-Dfp-
Thr-Ser-Cys]

(SEQ ID NO: 7)
Ala-Gly-c[Cys-Arg-Asn-Dfp-Phe-Trp-Lys-Thr-Dfp-
Ser-Ser-Cys]

(SEQ ID NO: 8)
Pro-c[Cys-Lys-Asn-Msa-Phe-Trp-Lys-Thr-Phe-Thr-
Ser-Cys]-Lys (SEQ ID NO: 9)
Pro-c[Cys-Lys-Asn-Phe-Msa-Trp-Lys-Thr-Phe-Thr-
Ser-Cys]-Lys (SEQ ID NO: 10)
Pro-c[Cys-Lys-Asn-Phe-Dfp-Trp-Lys-Thr-Phe-Thr-
Ser-Cys]-Lys (SEQ ID NO: 11)
Pro-c[Cys-Lys-Asn-Phe-Phe-Trp-Lys-Thr-Msa-Thr-
Ser-Cys]-Lys (SEQ ID NO: 12)
Pro-c[Cys-Arg-Asn-Msa-Phe-Trp-Lys-Thr-Msa-Thr-
Ser-Cys]-Lys (SEQ ID NO: 13)
Pro-c[Cys-Lys-Asn-Dfp-Phe-Trp-Lys-Thr-Msa-Ser-
Ser-Cys]-Lys (SEQ ID NO: 14)
Pro-c[Cys-Lys-Asn-Msa-Phe-Trp-Lys-Thr-Phe-Thr-
Ser-Cys]

(SEQ ID NO: 15)
Pro-c[Cys-Lys-Asn-Phe-Phe-Trp-Lys-Thr-Dfp-Thr-
Ser-Cys]

(SEQ ID NO: 16)
Met-Pro-c[Cys-Arg-Asn-Msa-Phe-Trp-Lys-Thr-Phe-
Ser-Ser-Cys]-Lys (SEQ ID NO: 17)
Asp-Arg-Met-Pro-c[Cys-Arg-Asn-Msa-Phe-Trp-Lys-
Thr-Phe-Thr-Ser-Cys]-Lys (SEQ ID NO: 18)
Asp-Arg-Met-Pro-c[Cys-Arg-Asn-Dfp-Phe-Trp-Lys-
Thr-Phe-Thr-Ser-Cys]-Lys

The person skilled in the art will understand that the amino acid sequences referred to in this invention may be chemically modified, for example, by means of chemical modifications that are physiologically relevant, such as phosphorylation, acetylation, amidation, PEGylation, n-octanoylation or palmitoylation, amongst others.

The compounds of this invention can exist as stereoisomers or mixtures of stereoisomers; for example, the amino acids forming them can have a L-, D-configuration, or be racemic independently of one another. Therefore, it is possible to obtain isomeric mixtures, as well as racemic mixtures or diastereomeric mixtures, or pure diastereomers or enantiomers, depending on the number of asymmetric carbons and on which isomers or isomeric mixtures are present. The preferred structures of the peptides of the invention are pure isomers, i.e. a single enantiomer or diastereomer.

For example, unless otherwise indicated, it is understood that the amino acid is L or D, or mixtures thereof, either racemic or non-racemic. The preparation processes described in this document allow the person skilled in the art to obtain each of the stereoisomers of the compound of the invention by choosing the amino acid with the suitable configuration. For example, the amino acid Trp can be L-Trp or D-Trp.

More preferably, the compounds included in formula (I) are selected from the group consisting of:

(SEQ ID NO: 4)
H-L-Ala-Gly-c[L-Cys-L-Lys-L-Asn-L-Phe-L-Dfp-D-Trp-
L-Lys-L-Thr-L-Phe-L-Thr-L-Ser-L-Cys]-OH (SEQ ID NO: 5)
H-L-Ala-Gly-c[L-Cys-L-Lys-L-Asn-L-Dfp-L-Phe-D-Trp-
L-Lys-L-Thr-L-Phe-L-Thr-L-Ser-L-Cys]-OH (SEQ ID NO: 6)
H-L-Ala-Gly-c[L-Cys-L-Lys-L-Asn-L-Phe-L-Phe-D-Trp-
L-Lys-L-Thr-L-Dfp-L-Thr-L-Ser-L-Cys]-OH (SEQ ID NO: 7)
H-L-Ala-Gly-c[L-Cys-L-Arg-L-Asn-L-Dfp-L-Phe-D-Trp-
L-Lys-L-Thr-L-Dfp-L-Ser-L-Ser-L-Cys]-OH (SEQ ID NO: 8)
H-L-Pro-c[L-Cys-L-Lys-L-Asn-L-Msa-L-Phe-D-Trp-L-
Lys-L-Thr-L-Phe-L-Thr-L-Ser-L-Cys]-L-Lys-OH (Octanoyl-SEQ ID NO: 8)
Octanoyl-L-Pro-c[L-Cys-L-Lys-L-Asn-L-Msa-L-Phe-D-
Trp-L-Lys-L-Thr-L-Phe-L-Thr-L-Ser-L-Cys]-L-Lys-OH -continued (SEQ ID NO: 9)
H-L-Pro-c[L-Cys-L-Lys-L-Asn-L-Phe-L-Msa-D-Trp-L-
Lys-L-Thr-L-Phe-L-Thr-L-Ser-L-Cys]-L-Lys-OH (Octanoyl-SEQ ID NO: 9)
Octanoyl-L-Pro-c[L-Cys-L-Lys-L-Asn-L-Phe-L-Msa-D-
Trp-L-Lys-L-Thr-L-Phe-L-Thr-L-Ser-L-Cys]-L-Lys-OH (Ac-SEQ ID NO: 10-NH$_2$)
Ac-L-Pro-c[L-Cys-L-Lys-L-Asn-L-Phe-L-Dfp-L-Trp-L-
Lys-L-Thr-L-Phe-L-Thr-L-Ser-L-Cys]-L-Lys-NH$_2$ (SEQ ID NO: 11)
H-L-Pro-c[L-Cys-L-Lys-L-Asn-L-Phe-L-Phe-D-Trp-L-
Lys-L-Thr-L-Msa-L-Thr-L-Ser-L-Cys]-L-Lys-OH (SEQ ID NO: 12)
H-L-Pro-c[L-Cys-L-Arg-L-Asn-L-Msa-L-Phe-D-Trp-L-
Lys-L-Thr-L-Msa-L-Thr-L-Ser-L-Cys]-L-Lys-OH (SEQ ID NO: 13-NH$_2$)
H-L-Pro-c[L-Cys-L-Lys-L-Asn-L-Dfp-L-Phe-L-Trp-L-
Lys-L-Thr-L-Msa-L-Ser-L-Ser-L-Cys]-L-Lys-NH$_2$ (SEQ ID NO: 14)
H-L-Pro-c[L-Cys-L-Lys-L-Asn-L-Msa-L-Phe-D-Trp-L-
Lys-L-Thr-L-Phe-L-Thr-L-Ser-L-Cys]-OH (Octanyol-SEQ ID NO: 14)
Octanoyl-L-Pro-c[L-Cys-L-Lys-L-Asn-L-Msa-L-Phe-D-
Trp-L-Lys-L-Thr-L-Phe-L-Thr-L-Ser-L-Cys]-OH (SEQ ID NO: 15)
H-L-Pro-c[L-Cys-L-Lys-L-Asn-L-Phe-L-Phe-D-Trp-L-
Lys-L-Thr-L-Dfp-L-Thr-L-Ser-L-Cys]-OH (SEQ ID NO: 16)
H-L-Met-L-Pro-c[L-Cys-L-Arg-L-Asn-L-Msa-L-Phe-D-
Trp-L-Lys-L-Thr-L-Phe-L-Ser-L-Ser-L-Cys]-L-Lys-OH (SEQ ID NO: 17)
H-L-Asp-L-Arg-L-Met-L-Pro-c[L-Cys-L-Arg-L-Asn-L-
Msa-L-Phe-L-Trp-L-Lys-L-Thr-L-Phe-L-Thr-L-Ser-L-
Cys]-L-Lys-OH (Myristoyl-SEQ ID NO: 17)
Myristoyl-L-Asp-L-Arg-L-Met-L-Pro-c[L-Cys-L-Arg-
L-Asn-L-Msa-L-Phe-L-Trp-L-Lys-L-Thr-L-Phe-L-Thr-
L-Ser-L-Cys]-L-Lys-OH (SEQ ID NO: 18)
H-Asp-L-Arg-L-Met-L-Pro-c[L-Cys-L-Arg-L-Asn-L-
Dfp-L-Phe-D-Trp-L-Lys-L-Thr-L-Phe-L-Thr-L-Ser-
L-Cys]-L-Lys-OH The pharmaceutically acceptable salts of the compounds provided by this invention are also found within the field of this invention. The term "pharmaceutically acceptable salts" means a salt recognized for its use in animals and more specifically in human beings, and includes salts used to form base addition salts, whether they are inorganic, for example and not restricted to, lithium, sodium, potassium, calcium, magnesium, manganese, copper, zinc or aluminium, amongst others, whether they are organic, for example and not restricted to, ethylamine, diethylamine, ethylenediamine, ethanolamine, diethanolamine, arginine, lysine, histidine or piperazine among others, or acid addition salts, whether they are organic, for example and not restricted to, acetate, citrate, lactate, malonate, maleate, tartrate, fumarate, benzoate, aspartate, diaspartate, triaspartate, glutamate, succinate, oleate, trifluoroacetate, oxalate, pamoate or gluconate amongst others, or inorganic, for example and not restricted to, chloride, sulfate, borate or carbonate amongst others. The nature of the salt is not critical, provided that it is pharmaceutically acceptable. The pharmaceutically acceptable salts of the compounds of the invention can be obtained by conventional methods that are well known in prior art [Berge S. M. et al., *J. Pharm. Sci.* 1977, 66, 1-19].

Preparation Process

Synthesis of the compounds of this invention, their stereoisomers, or their pharmaceutically acceptable salts can be carried out according to conventional methods, known in the state of the art.

In an embodiment of this invention, the compounds are synthesized using solid phase peptide synthesis methods or synthesis in solution.

The solid phase synthesis methods are described for example in [Stewart J. M. and Young J. D., 1984, *"Solid Phase Peptide Synthesis, 2nd edition"* Pierce Chemical Company, Rockford, Illinois; Bodanzsky M., and Bodanzsky A., 1984 *"The practice of Peptide Synthesis"* Springer Verlag, Berlin; Lloyd-Williams P., Albericio F. and Giralt E. (1997) *"Chemical Approaches to the Synthesis of Peptides and Proteins"* CRC, Boca Raton, FL, USA]. Synthesis in solution methods and combinations of solid phase synthesis and in solution methods or enzymatic synthesis are described in [(Kullmann W. et al., *J. Biol. Chem.* 1980, 255, 8234-8238].

In an embodiment of this invention, the compounds of formula (I), their stereoisomers, mixtures thereof, or their cosmetically or pharmaceutically acceptable salts are prepared by means of a method comprising the following procedure:

1. Solid phase synthesis
2. Cleavage of the peptide from the polymeric support
3. Cyclization of the peptide in solution
4. Removal of the protecting groups or alternatively, 1. Solid phase synthesis
2. Solid phase cyclization
3. Cleavage of the peptide from the polymeric support and simultaneous removal of the protecting groups, preferably via treatment with trifluoroacetic acid.

Preferably, the C-terminal end is bound to a solid support and the procedure is carried out in solid phase and therefore, comprises the coupling of an amino acid with the N-terminal end protected and the C-terminal end free on an amino acid with the N-terminal end free and the C-terminal end bound to a polymeric support; removal of the protecting group of the N-terminal end; and repetition of this sequence as many times as needed to thus obtain the peptide, preferably of 13 to 17 amino acids, finally followed by the cleavage of the synthesized peptide from the original polymeric support.

The functional groups of the side chains of the amino acids remain conveniently protected by temporary or permanent protecting groups throughout synthesis, and may be deprotected simultaneously or orthogonally in the cleavage process of the peptide from the polymeric support.

Alternatively, solid phase synthesis can be carried out by using a convergent strategy by coupling a peptide fragment on the polymeric support or on a peptide fragment previously bound to the polymeric support. Convergent synthesis strategies are widely known by persons skilled in the art and are described in Lloyd-Williams P. et al., *Tetrahedron* 1993, 49, 11065-11133.

The process can include the additional stages of deprotecting the N-terminal and C-terminal ends and/or cleaving the peptide from the polymeric support in an indistinct order, using standard procedures and conditions known in the art, after which the functional groups of said ends can be modified. The optional modification of the N-terminal and C-terminal ends can be carried out with the peptide of formula (I) anchored to the polymeric support or once the peptide has been cleaved from the polymeric support.

Optionally, $R_1$ can be introduced by reacting the N-terminal end of the peptide of the invention with an $R_1$—Z compound, wherein $R_1$ has the aforementioned meaning and Z is a leaving group, for example and not restricted to, the tosyl group, the mesyl group and halogen groups amongst others; through a nucleophilic substitution reaction, in the presence of a suitable base and solvent, wherein the fragments possess the functional groups that are not involved in the N—C bond formation and are conveniently protected with temporary or permanent protecting groups. $R_1$ may also be introduced by the reaction of the N-terminal end of the compound of the invention with a $R_5$COOH group or its esters, acid halides or its anhydride.

Optionally and/or additionally, the $R_2$ radicals can be introduced by the reaction of a $HR_2$ compound wherein $R_2$ is —$OR_3$, —$NR_3R_4$ or —$SR_3$, with a complementary fragment which corresponds to the peptide of formula (I) in which $R_2$ is —OH in the presence of an appropriate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, an uronium salt, a phosphonium salt or an amidinium salt, amongst others, to thereby obtain a peptide according to the invention of general formula (I), wherein said fragments possess functional groups that are not involved in the N—C, O—C or S—C bond formation and are suitably protected with temporary or permanent protecting groups. Alternatively other $R_2$ radicals can be incorporated simultaneously to the peptide cleavage process from the polymeric support.

A person skilled in the art would easily understand that the stages of deprotection/cleavage of the C-terminal and N-terminal ends and their subsequent derivatization can be performed in an indistinct order, according to the processes known in prior art. [Smith M. B. and March J., 1999 "*March's Advanced Organic Chemistry Reactions, Mechanisms and Structure*", 5th Edition, John Wiley & Sons, 2001].

The term "protecting group" relates to a group which blocks an organic functional group and which can be removed in controlled conditions. The protecting groups, their relative reactivities and the conditions in which they remain inert are known by the person skilled in the art.

Examples of representative protecting groups for the amino group are amides, such as amide acetate, amide benzoate, amide pivalate; carbamates such as benzyloxycarbonyl (Cbz or Z), 2-chlorobenzyl (CIZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), trityl (Trt), methoxytrityl (Mtt), 2,4-dinitrophenyl (Dnp), N-[1-(4,4-dimethyl-2,6-dioxocyclohex-1-ylidene)ethyl](Dde), 1-(4,4-dimethyl-2,6-dioxo-cyclohexylidene)-3-methylbutyl (ivDde), 1-(1-adamantyl)-1-methylethoxycarbonyl (Adpoc), amongst others; preferably Boc or Fmoc.

Examples of representative protecting groups for the carboxyl group are esters, such as the tert-butyl ester (tBu), allyl ester (All), triphenylmethyl ester (trityl ester, Trt), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino) benzyl ester (Dmab), amongst others; preferred protecting groups of the invention are the All, tBu, cHex, Bzl and Trt esters.

Trifunctional amino acids can be protected during the synthetic process with temporary or permanent protecting groups orthogonal to the protecting groups of the N-terminal and C-terminal ends. To protect the amino group of the lysine side chain, the protectors of the abovementioned amino group are used. The tryptophan side chain can be protected by any of the protecting groups of the abovementioned amino groups or can be used unprotected. The threonine and serine side chain can be protected with a tert-butyl ester (tBu). The cysteine side chain can be protected by a protecting group selected from the group consisting of trityl and acetamidomethyl. The asparagine side chain can be protected by a protecting group selected from the group consisting of methoxytrityl, trityl or xanthyl or can be used unprotected. The arginine side chain is protected with a protecting group selected from the group consisting of tosyl (Tos), 4-methoxy-2,3,6-trimethylbenzenesulfonyl (Mtr), Alloc, nitro, 2,2,4,6,7-pentamethyldihydrobenzofuran-5-sulfonyl (Pbf) and 2,2,5,7,8-pentamethylchroman-6-sulfonyl (Pmc). The methionine side chain is used protected with the sulphoxide group or used unprotected. The aspartic acid side chain is protected with a protecting group selected from the group consisting of Trt, Bzl, cHx, tBu and All. The preferred protecting groups of trifunctional amino acids of the invention are tBu esters in the serine and threonine side chains; Boc in the lysine side chains, Trt in the cysteine side chains; Pbf in the arginine side chains and Fmoc or Boc as the temporary protecting group of the N-terminal end.

Examples of these and additional protective groups, their introduction and removal, can be found in literature [Greene T. W. and Wuts P. G. M., (1999) "*Protective groups in organic synthesis*" John Wiley & Sons, New York; Atherton B. and Sheppard R. C. (1989) "*Solid Phase Peptide Synthesis: A practical approach*" IRL Oxford University Press]. The term "protecting groups" also includes the polymeric supports used in solid phase synthesis.

When the synthesis is performed totally or partially in solid phase, the possible solid supports used in the procedure of the invention can involve polystyrene supports, polyethylene glycol grafted to polystyrene and such like, for example and not restricted to, p-methylbenzhydrylamine resins (MBHA) [Matsueda G. R. et al, *Peptides* 1981, 2, 45-50], 2-chlorotrityl resins [Barlos K. et al. 1989 *Tetrahedron Lett.* 30:3943-3946; Barlos K. et al, 1989 *Tetrahedron Lett.* 30, 3947-3951], TentaGel® resins (Rapp Polymere GmbH), ChemMatrix® resins (Matrix Innovation, Inc) and such like, which may or may not include a labile linker, such as 5-(4-aminomethyl-3,5-dimethoxyphenoxy) valeric acid (PAL) [Albericio F. et al, 1990, *J. Org. Chem.* 55, 3730-3743], 2-[4-aminomethyl-(2,4-dimethoxyphenyl)]phenoxyl acetic acid (AM) [Rink H., 1987, *Tetrahedron Lett.* 28, 3787-3790], Wang [Wang S. S., *J. Am. Chem. Soc.*, 1973, 95, 1328-1333] and such like, which enable cleavage of the semi-protected peptide and formation of the cycle in solution with a deprotection step in solution or even solid phase cyclisation and the subsequent simultaneous deprotection and cleavage of the peptide.

Pharmaceutical Compositions

The compounds of the invention can be administered by any means that cause contact between the compounds and their action site in a mammal's body, preferably that of a human being, and in the form of a composition which contains them.

To this regard, another aspect of the invention is a pharmaceutical composition which comprises a pharmaceutical effective amount of at least one compound of general formula (I), its stereoisomers, mixtures thereof, and/or its pharmaceutically acceptable salts. The pharmaceutical composition of the invention can include the compound of the general formula (I), its stereoisomers, mixtures thereof, and/or its solid pharmaceutically acceptable salts obtained by freeze-drying or spray-drying, and can be reconstituted in a solvent suitable for its administration.

The pharmaceutical composition of the invention can comprise at least one pharmaceutically acceptable excipient. The number and nature of the pharmaceutically acceptable excipients depend on the administration method desired. Pharmaceutically acceptable excipients are well known by experts in the field [Rowe R. C., Sheskey P. J., Quinn, M. E. (2009) *"Handbook of Pharmaceutical Excipients, 6th Edition", Pharmaceutical Press and American Pharmacists Association*]. Said compositions may be prepared using the conventional methods that are known in the state of the art.

The compounds of this invention have variable solubility in water, according to the nature of their sequence of amino acids or any possible modifications on their N-terminal and/or C-terminal ends. Therefore, the compounds of this invention can be incorporated into the compositions by means of an aqueous solution, and those which are not soluble in water can be solubilized in pharmaceutically acceptable conventional solvents such as and not restricted to, ethanol, propanol, isopropanol, propylene glycol, glycerin, dimethyl sulfoxide, butylene glycol or polyethylene glycol or any combination thereof.

The pharmaceutically effective amount of the compounds of the invention which must be administered, and their dosage, will depend on numerous factors, including age, state of the patient, the nature or severity of the disorder or disease to be treated or prevented, the route and frequency of administration as well as on the specific nature of the compounds to be used.

"Pharmaceutically effective amount" is understood to mean a non-toxic but sufficient amount of the compound of the invention to provide the desired effect.

The compounds of the invention are used in the pharmaceutical composition of this invention at pharmaceutically effective concentrations to achieve the desired effect; in their preferred form, the efficient daily dosage in humans is between 0.1 mg and 1000 mg/day, preferably between 0.5 and 100 mg/day and even more preferably between 1 and 10 mg/day.

The frequency of administration of the pharmaceutical composition can be, for example and not limited to, monthly, fortnightly, weekly, twice a week, three times a week or daily.

The compounds of the invention, their stereoisomers, mixtures thereof and/or their cosmetic or pharmaceutically acceptable salts, can also be incorporated into delivery systems and/or pharmaceutical sustained release systems.

The term "delivery systems" relates to a diluent, adjuvant excipient or carrier with which the peptide of the invention is administered. These pharmaceutical carriers can be liquids, such as water, oils or surfactants, including those of petroleum, animal, plant or synthetic origin, for example and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and such. A person skilled in the art knows the diluents, adjuvants or excipients which can be used in the different delivery systems in which the compounds of the invention can be administered.

The term "sustained release" is used in a conventional sense referring to a delivery system of a compound which provides the gradual release of said compound during a period of time and preferably, although not necessarily, with relatively constant compound release levels over a period of time.

Examples of delivery or sustained release systems include, without restriction, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules and nanocapsules, as well as in microemulsions and nanoemulsions, which can be added to achieve a greater bioavailability of the active principle and/or improve its pharmacokinetic and pharmacodynamic properties.

The pharmaceutical compositions of the compounds of the invention, their stereoisomers, mixtures thereof, and/or their pharmaceutically acceptable salts can be administered by any appropriate route, for which the pharmaceutically acceptable excipients necessary for the formulation of the administration form desired will be included, by local or systematic application, for example and not limited to, topical, enteral or parenteral route. In the context of this invention, the term "topical" route includes dermal and ophthalmic routes, the term "enteral" route includes administration to the digestive system such as oral, buccal, gastric, sublingual and rectal routes and the term "parenteral" refers to nasal, auricular, ophthalmic, vaginal, subcutaneous injections, intradermal, intravascular for example intravenous, intramuscular, intraocular, intraspinal, intracranial, intraarticular, intrathecal and intraperitoneal routes, as well as any other similar injection or infusion technique. Treatment in vitro is also considered, for example, in damaged cells cultures and/or stem cells and the ex vivo treatment.

More specifically, the treatment, prevention and/or diagnosis with the compounds and compositions of this invention, is carried out in vivo as the preferred administration route is subcutaneous.

In a more particular aspect, the pharmaceutical compositions of this invention comprise other therapeutic agents, for example and not restricted to, other anti-inflammatory, immunosuppressive agents or metabolic or enzyme inhibitors, non-steroidal anti-inflammatory agents (NSAIDs) such as ibuprofen, tenidap, naproxen, meloxicam, mesalazine, piroxicam, diclofenac, indomethacin and sulfasalazine, corticosteroids such as prednisolone, hydrocortisone, beclomethasone, budesonide; cytokine-suppressant anti-inflammatory drugs (CSAID), nucleotide synthesis inhibitors, such as methotrexate and leflunomide, immunosuppressors such as cyclosporin, tacrolimus (FK-506), mTOR inhibitors such as sirolimus (rapamycin) or derivatives of rapamycin, tumor necrosis factor (TNFα) inhibiting agents such as infliximab, adalimumab, etanercept, certolizumab, golimumab, COX-2 inhibitors like celecoxib, rofecoxib, valdecoxib and variants thereof, phosphodiesterase inhibitors, phospholipase inhibitors such as trifluoromethyl ketone analogues, vascular endothelial growth factor inhibitors or growth factor receptor inhibitors, angiogenesis inhibitors, natalizumab (anti alpha 4 integrin), rituximab (anti-CD20), abatacept (anti-CD80 and CD86), fostamatinib (spleen tyrosine kinase Syk inhibitor), tocilizumab (anti IL-6), anakinra (anti IL-1), tofacitinib (Janus kinase inhibitor), 6-mercaptopurines (6-MP), azathioprine, balsalazide, sulfasalazine, mesalazine, olsalazine, chloroquine, hydroxychloroquine, penicillamine, auranofin, aurothiomalate, azathioprine, colchicine, beta-2 adrenergic receptor agonists such as salbutamol, terbutaline and salmeterol, xanthines such as theophylline andaminophylline, cromoglycate, nedocromil, ketotifen, ipratropium, oxitropium, mycophenolate mofetil, adenosine agonists, anti-thrombosis agents, penicillin, complement inhibitors and adrenergic agents.

Uses

Regarding another aspect, this invention refers to a compound of general formula (I), its stereoisomers, mixtures thereof and/or its pharmaceutically acceptable salts for use in medicine.

Another aspect of this invention refers to a compound of general formula (I), its stereoisomers, mixtures thereof and/or its pharmaceutically acceptable salts, for the treatment, prevention and/or diagnosis of those conditions, disorders and/or pathologies where the somatostatin receptors sstr1, sstr2, sstr3, sstr4 and/or sstr5, and/or the ghrelin receptor and/or a specific cortistatin receptor or combinations thereof are expressed.

In a more particular aspect, this invention refers to a compound of general formula (I), its stereoisomers, mixtures thereof and/or its pharmaceutically acceptable salts, for the treatment, prevention and/or diagnosis of those conditions, disorders and/or pathologies selected from the group consisting of diseases of the immune system, inflammatory pathologies, tumours, cancer, neurodegenerative diseases, eye diseases, respiratory disorders, infections, pain, healing wounds, tissue regeneration, septic disorders and disorders related with transplants/organ or tissue grafts.

In an additional particular aspect, this invention refers to a compound of general formula (I), its stereoisomers, mixtures thereof and/or its pharmaceutically acceptable salts, for the treatment, prevention and/or diagnosis of those conditions, disorders and/or pathologies selected from the group consisting of endotoxemia, septic shock, toxic shock syndrome, sepsis, inflammatory bowel disease, Crohn's disease, chronic colitis, ulcerative colitis, autoimmune gastritis, rheumatoid arthritis, osteoarthritis, multiple sclerosis, diarrhea, grade 3-4 diarrhea, diarrhea associated with radiotherapy and/or chemotherapy treatments, symptomatic treatment of carcinoid syndrome or VIPoma, endocrine cancer, pancreatic cancer, chronic pancreatitis, acromegaly, symptomatic treatment of gastroenteropancreatic neuroendocrine tumours, esophageal varices, hypertrophic pulmonary osteoarthropathy and thyrotropic adenoma, colorectal cancer, breast cancer, ovarian cancer, prostate cancer, thyroid cancer, lung cancer, stomach cancer, hepatocellular carcinoma, Alzheimer, arthritis, allergies, Lupus, Lupus erythematosus, lymphoproliferative disorder, diabetic retinopathy, macular edema, Graves ophthalmopathy, Cushing's syndrome, neuropathic pain, restenosis, angiogenesis, hyperthyroidism, hypothyroidism, hyperinsulinemia, hypocalcaemia, Paget's disease, cachexia and Zollinger-Ellison syndrome, pyoderma gangrenosum, thyropathy, type 1 insulin dependent diabetes mellitus, Hashimoto's thyroiditis, Graves disease, autoimmune hepatitis, allergic encephalomyelitis, uveoretinitis, uveitis, transplant rejection, graft rejection, graft-versus-host disease, Libman-Sacks endocarditis, mixed connective tissue disease, scleroderma, dermatopolymyositis, Wegener granulomatosis, Sjögren's syndrome, granuloma, lichen sclerosus, primary biliary cirrhosis, keratitis, glomerulonephritis, reactive arthritis, synovialitis, Reiter's syndrome, Lime's disease, psoriatic arthritis, induced arthritis, ankylosing spondylitis, myasthenia gravis, vasculitis, autoimmune thyroiditis, allergies, dermatitis or eczema, psoriasis, psoriasis, dermatitis fibrosis, chronic obstructive pulmonary disease (COPD), encephalomyelitis, autoimmune thyroiditis, aged ulcer, iritis, conjunctivitis, keratoconjunctivitis, spondyloarthropathy, vaginitis, proctitis, drug eruptions, leprosy reversal reactions, erythema nodosum leprosum, acute necrotizing hemorrhagic encephalopathy, idiopathic progressive bilateral sensorineural hearing loss, aplastic anemia, pure red cell anemia, idiopathic thrombocytopenia, polychondritis, chronic active hepatitis, Stevens-Johnson syndrome, idiopathic sprue, lichen planus and sarcoidosis.

Another embodiment of this invention refers to the use of a compound of general formula (I), its stereoisomers, mixtures thereof and/or its pharmaceutically acceptable salts, in the preparation of a pharmaceutical composition for the treatment, prevention and/or diagnosis of those conditions, disorders and/or pathologies where the somatostatin receptors sstr1, sstr2, sstr3, sstr4 and/or sstr5, and/or the ghrelin receptor and/or a specific cortistatin receptor or combinations thereof are expressed.

In a more particular aspect, this invention refers to the use of a compound of general formula (I), its stereoisomers, mixtures thereof and/or its pharmaceutically acceptable salts, in the preparation of a pharmaceutical composition for the treatment, prevention and/or diagnosis of those conditions, disorders and/or pathologies selected from the group consisting of diseases of the immune system, inflammatory disorders, tumours, cancer, neurodegenerative diseases, eye diseases, respiratory diseases, infections, pain, healing wounds, tissue regeneration, septic disorders and disorders related to transplants/organ or tissue grafts.

In a more particular aspect, this invention refers to the use of a compound of general formula (I), its stereoisomers, mixtures thereof and/or its pharmaceutically acceptable salts, in the preparation of a pharmaceutical composition for the treatment, prevention and/or diagnosis of those conditions, disorders and/or pathologies selected from the group consisting of endotoxemia, septic shock, toxic shock syndrome, sepsis, inflammatory bowel disease, Crohn's disease, chronic colitis, ulcerative colitis, autoimmune gastritis, rheumatoid arthritis, osteoarthritis, multiple sclerosis, diarrhea, grade 3-4 diarrhea, diarrhea associated with radiotherapy and/or chemotherapy treatments, symptomatic treatment of carcinoid syndrome or VIPoma, endocrine cancer, pancreatic cancer, chronic pancreatitis, acromegaly, symptomatic treatment of gastroenteropancreatic neuroendocrine tumours, esophageal varices, hypertrophic pulmonary osteoarthropathy and thyrotropic adenoma, colorectal cancer, breast cancer, ovarian cancer, prostate cancer, thyroid cancer, lung cancer, stomach cancer, hepatocellular carcinoma, Alzheimer, arthritis, allergies, Lupus, Lupus erythematosus, lymphoproliferative disorder, diabetic retinopathy, macular edema, Graves ophthalmopathy, Cushing's syndrome, neuropathic pain, restenosis, angiogenesis, hyperthyroidism, hypothyroidism, hyperinsulinemia, hypercalcaemia, Paget's disease, cachexia and Zollinger-Ellison syndrome, pyoderma gangrenosum, thyropathy, type 1 insulin dependent diabetes mellitus, Hashimoto's thyroiditis, Graves disease, autoimmune hepatitis, allergic encephalomyelitis, uveoretinitis, uveitis, transplant rejection, graft rejection, graft-versus-host disease, Libman-Sacks endocarditis, mixed connective tissue disease, scleroderma, dermatopolymyositis, Wegener granulomatosis, Sjögren's syndrome, granuloma, lichen sclerosus, primary biliary cirrhosis, keratitis, glomerulonephritis, reactive arthritis, synovialitis, Reiter's syndrome, Lime's disease, psoriatic arthritis, induced arthritis, ankylosing spondylitis, myasthenia gravis, vasculitis, allergies, dermatitis or eczema, psoriasis, dermatitis fibrosis, chronic obstructive pulmonary disease (COPD), encephalomyelitis, autoimmune thyroiditis, aged ulcer, iritis, conjunctivitis, keratoconjunctivitis, spondyloarthropathy, vaginitis, proctitis, drug eruptions, leprosy reversal reactions, erythema nodosum leprosum, acute necrotizing hemorrhagic encephalopathy, idiopathic progressive bilateral sensorineural hearing loss, aplastic anemia, pure red cell anemia, idiopathic thrombocytopenia, polychondritis, chronic active hepatitis, Stevens-Johnson syndrome, idiopathic sprue, lichen planus and sarcoidosis.

An additional aspect of this invention refers to a method for the treatment, prevention and/or diagnosis of those conditions, disorders and/or pathologies where somatostatin receptors sstr1, sstr2, sstr3, sstr4 and/or sstr5, and/or the ghrelin receptor and/or a specific cortistatin receptor or combinations thereof are expressed, which comprises the administration of a pharmaceutically effective amount of at least one compound of general formula (I), its stereoisomers, mixtures thereof and/or its pharmaceutically acceptable salts.

In another particular aspect, this invention refers to a method for the treatment, prevention and/or diagnosis of those conditions, disorders and/or pathologies selected from the group consisting of diseases of the immune system, inflammatory disorders, tumours, cancer, neurodegenerative diseases, eye diseases, respiratory diseases, infections, pain, healing wounds, tissue regeneration, septic disorders and disorders related to transplants/organ or tissue grafts, which comprises the administration of a pharmaceutically effective amount of at least one compound of general formula (I), its stereoisomers, mixtures thereof and/or its pharmaceutically acceptable salts.

In another particular aspect, this invention refers to a method for the treatment, prevention and/or diagnosis of those conditions, disorders and/or pathologies selected from the group consisting of endotoxemia, septic shock, toxic shock syndrome, sepsis, inflammatory bowel disease, Crohn's disease, chronic colitis, ulcerative colitis, autoimmune gastritis, rheumatoid arthritis, osteoarthritis, multiple sclerosis, diarrhea, grade 3-4 diarrhea, diarrhea associated with radiotherapy and/or chemotherapy treatments, symptomatic treatment of carcinoid syndrome or VIPoma, endocrine cancer, pancreatic cancer, chronic pancreatitis, acromegaly, symptomatic treatment of gastroenteropancreatic neuroendocrine tumours, esophageal varices, hypertrophic pulmonary osteoarthropathy and thyrotropic adenoma, colorectal cancer, breast cancer, ovarian cancer, prostate cancer, thyroid cancer, lung cancer, stomach cancer, hepatocellular carcinoma, Alzheimer, arthritis, allergies, Lupus, Lupus erythematosus, lymphoproliferative disorder, diabetic retinopathy, macular edema, Graves ophthalmopathy, Cushing's syndrome, neuropathic pain, restenosis, angiogenesis, hyperthyroidism, hypothyroidism, hyperinsulinemia, hypercalcaemia, Paget's disease, cachexia and Zollinger-Ellison syndrome, pyoderma gangrenosum, thyropathy, type 1 insulin dependent diabetes mellitus, Hashimoto's thyroiditis, Graves disease, autoimmune hepatitis, allergic encephalomyelitis, uveoretinitis, uveitis, transplant rejection, graft rejection, graft-versus-host disease, Libman-Sacks endocarditis, mixed connective tissue disease, scleroderma, dermatopolymyositis, Wegener granulomatosis, Sjögren's syndrome, granuloma, lichen sclerosus, primary biliary cirrhosis, keratitis, glomerulonephritis, reactive arthritis, synovialitis, Reiter's syndrome, Lime's disease, psoriatic arthritis, induced arthritis, ankylosing spondylitis, myasthenia gravis, vasculitis, allergies, dermatitis or eczema, psoriasis, dermatitis fibrosis, chronic obstructive pulmonary disease (COPD), encephalomyelitis, autoimmune thyroiditis, aged ulcer, iritis, conjunctivitis, keratoconjunctivitis, spondyloarthropathy, vaginitis, proctitis, drug eruptions, leprosy reversal reactions, erythema nodosum leprosum, acute necrotizing hemorrhagic encephalopathy, idiopathic progressive bilateral sensorineural hearing loss, aplastic anemia, pure red cell anemia, idiopathic thrombocytopenia, polychondritis, chronic active hepatitis, Stevens-Johnson syndrome, idiopathic sprue, lichen planus and sarcoidosis, which comprises the administration of a pharmaceutically effective amount of at least one compound of general formula (I), its stereoisomers, mixtures thereof and/or its pharmaceutically acceptable salts.

EXAMPLES

The following specific examples provided in this patent document serve to illustrate the nature of the present invention. These examples are included only for illustrative purposes and must not be interpreted as being limitations to the invention claimed herein.

Abbreviations

The abbreviations used in the present description have the following meanings:

$Ac_2O$, Acetic anhydride; AcOH, Acetic acid; Adpoc, 1-(1-adamantyl)-1-methylethoxy-carbonyl; AII, allyl; Alloc, allyloxycarbonyl; Boc, tert-butyloxycarbonyl; Bzl, benzyl; Cbz, benzyloxycarbonyl; cHx, cyclohexyl; ClZ, 2-chlorobenzyl; CST, cortistatin; DCM, Dichloromethane; Dde, N-[1-(4,4-dimethyl-2,6-dioxocyclohex-1-ylidene)ethyl]; DMEM, Dulbecco's modified Eagle's medium; Dfp, 3,5-difluorophenylalanine; DIEA, N,N'-diisopropylethylamine; DIPCDI, Diisopropylcarbodiimide; Dmab, 4-(N-[1-(4,4-dimethyl-2,6-dioxocyclohexylidene)-3-methylbutyl]amino) benzyl; DMF, N,N-dimethylformamide; Dnp, 2,4-dinitrophenyl; DOTA, 1,4,7,10-tetraazacyclododecane-1,4,7,10-tetraacetic acid; DTPA, Diethylenetriaminepentaacetic acid; ESI-MS, electrospray ionization mass spectrometry; Fm, fluorenylmethyl; Fmoc, 9-fluorenylmethyloxycarbonyl; HF, Hydrofluoric acid; HOBT, N-hydroxybenzotriazole; HPLC, high performance liquid chromatography; IC50, half maximal inhibitory concentration; ivDde, 1-(4,4-dimethyl-2,6-dioxocyclohexylidene)-3-methyl-butyl; Ki, inhibition constant of a drug; LPS, lipopolysaccharide; M, molecular mass; Mtt, methoxytrityl; μL, microlitre; pmol, micromole; pNZ, p-nitrobenzyloxycarbonyl; RP-HPLC, Reverse Phase HPLC; SST, somatostatin; sstr, somatostatin receptors; tBu, tert-butyl; Teoc, 2-(trimethylsilyl)ethyloxycarbonyl; TFA, trifluoroacetic acid; TFE, 2,2,2-trifluoroethanol; TIS, triisopropylsilane; tr, retention time; Trt, trityl; Troc, 2,2,2-trichloroethyloxycarbonyl; Z, benzyloxycarbonyl.

Example 1: Synthesis of Compound 1

(SEQ ID NO: 9
H-L-Pro-c[L-Cys-L-Lys-L-Asn-L-Phe-L-Msa-D-Trp-L-

Lys-L-Thr-L-Phe-L-Thr-L-Ser-L-Cys-]-L-Lys-OH

The resin was placed in a synthesis reactor equipped with a filtering plate and a key. The incorporation of the C-terminal residue was carried out on 0.25 g of 2-chlorotrityl resin (1.6 mmol/g). The first amino acid, Fmoc-Lys(Boc)-OH (1 eq.) was dissolved in 1.25 ml of DCM and 75 μL of DMF. DIEA (3 eq.) was added. The solution with amino acid and base was transferred to the reactor and stirred for 45 minutes. After this, 0.2 mL of MeOH was added and left to react for 10 minutes. It was filtered out and the filtrate discarded. The resin was washed with DCM and DMF. In each wash, the filtrates were filtered out and discarded. In order to incorporate the following amino acids, 2.5 eq. of Fmoc-amino acid, 2.5 eq. HOBT and 2.5 eq. DIPCDI were used. For the coupling reaction, it was left to react for 40-60 minutes and the incorporation of the amino acid was controlled with a ninhydrine test. If the ninhydrine test was positive, a reactivation stage was undertaken for 15-30 minutes with 0.83 eq. of HOBT and 0.83 eq. DIPCDI. If the ninhydrine test was still positive, re-coupling was carried out with 1.25 eq. of Fmoc-amino acid, HOBT and DIPCDI. If the ninhydrine test was negative, synthesis proceeded with the step of deprotecting the Fmoc group by treatment with a solution of 20% piperidine in DMF twice. The peptidyl-resin was washed 5 times with DMF, filtering out and discarding the filters each time, and the next amino acid was then incorporated. The N-terminal amino acid was incorporated in the form of Boc-Pro-OH. 1.03 g of peptide-resin was obtained.

1.03 g (0.3 mmol) of peptidyl-resin were deposited in a reactor. 9.6 mL of an AcOH: TFE: DCM solution were added during magnetic stirring and left to react for 2 hours. It was filtered in a reactor with a filter plate and the filtrate was recovered. The resin was washed 3 times with 2.55 mL of the AcOH: TFE: DCM solution and the filtrates were recovered.

A solution of 0.73 g (10 eq.) iodine in 3.57 mL of AcOH: TFE: DCM solution was prepared. The filtrates recovered in the acidolysis were transferred to the reactor that contained the iodine solution and were left to react under stirring. A solution of 1.52 g (22 eq.) sodium thiosulfate in 6.12 mL of water was prepared and added to the reactor once oxidation was complete, and a complete decolouration was observed in 5 minutes. The stirring was stopped and the mixture was allowed to decant until phase separation. An extraction was carried out by treating the aqueous phase with DCM 3 times and the organic phase with 5% citric acid: NaCl (v:w). The organic fractions were evaporated and the residue vacuum dried. The solid residue was washed with water in a filter plate. 0.73 g of protected oxidised product were obtained.

6.8 mL of the cocktail of the reaction TFA:$H_2$O:DCM: anisole (55:5:30:10) was added to the reactor. 0.73 g of the oxidized and protected peptide was added to the previous solution and it was left to react for 4 hours. Heptane (13 mL) was added and it was stirred for 5 minutes. The stirring was stopped and it was left to decant. The aqueous phase was poured on cold ether and left to rest for 15-30 minutes. The obtained suspension was filtered through a filter plate and the filtrates discarded. The residue was washed with ether discarding the filtrates from each washing. The solid was freeze-dried and 0.56 g of crude product obtained.

The crude product was purified in a semipreparative system equipped with a NW50 column filled with 10 micrometers of kromasil silica. The peptide was suspended in 0.1N AcOH and DOWEX resin prepared in 0.1N AcOH was added. The final acetate compound was recovered via filtering and was characterized by mass spectrometry in an ESI-MS equipment.

Characterization: ESI-MS: Theoretical M=1777.1 g/mol, Experimental M: (m/z): [M+2H]$^+$/2=889.3, [M+3H]$^+$/3=593.1

Example 2: Synthesis of Compound 2

```
                              (Octanoyl-SEQ ID NO: 9)
Octanoyl-L-Pro-c[L-Cys-L-Lys-L-Asn-L-Phe-L-Msa-D-

Trp-L-Lys-L-Thr-L-Phe-L-Thr-L-Ser-L-Cys-]-L-Lys-OH
```

The compound was prepared using the method described in example 1. 0.25 g of resin were used to start and the same equivalent ratios were used. The N-terminal amino acid was added in the form of Fmoc-Pro-OH. The octanoyl acid was introduced into the sequence using 5 eq. of acid, 5 eq. of HOBT and 5 eq. of DIPCDI. 0.5 g of crude product were obtained.

Characterization: ESI-MS: Theoretical M=1903.35 g/mol, Experimental M: (m/z): [M+2H]$^+$/2=952.4, [M+3H]$^+$/2=635.2

Example 3: Synthesis of Compound 3

```
                              (SEQ ID NO: 8)
H-L-Pro-c[L-Cys-L-Lys-L-Asn-L-Msa-L-Phe-D-Trp-L-

Lys-L-Thr-L-Phe-L-Thr-L-Ser-L-Cys]-L-Lys-OH
```

The compound was prepared using the method described in example 1. 0.25 g of resin and the same equivalent ratios were used. The N-terminal amino acid was added in the form of Boc-Pro-OH. 0.53 g of crude product were obtained.

Characterization: ESI-MS: Theoretical M=1777.15 g/mol, Experimental M: (m/z): [M+2H]$^+$/2=889.3 [M+3H]$^+$/2=593.1

Example 4: Synthesis of Compound 4

```
                              (Octanoyl-SEQ ID NO: 8)
Octanoyl-L-Pro-c[L-Cys-L-Lys-L-Asn-L-Msa-L-Phe-D-

Trp-L-Lys-L-Thr-L-Phe-L-Thr-L-Ser-L-Cys-]-L-Lys-OH
```

The compound was prepared using the method described in example 1. 0.25 g of resin and the same equivalent ratios were used. The N-terminal amino acid was added in the form of Fmoc-Pro-OH. The octanoyl acid was introduced into the sequence using 5 eq. of acid, 5 eq of HOBT and 5 eq. of DIPCDI. 0.55 g of crude product were obtained.

Characterization: ESI-MS: Theoretical M=1903.35 g/mol, Experimental M: (m/z): [M+2H]$^+$/2=952.4, [M+3H]$^+$/2=635.2

Example 5: Synthesis of Compound 5

```
                              (Octanoyl-SEQ ID NO: 14)
Octanoyl-L-Pro-c[L-Cys-L-Lys-L-Asn-L-Msa-L-Phe-D-

Trp-L-Lys-L-Thr-L-Phe-L-Thr-L-Ser-L-Cys]-OH
```

The compound was prepared using the method described in example 1. 0.4 g of resin and the same equivalent ratios were used. The N-terminal amino acid was added in the form of Fmoc-Pro-OH. The octanoyl acid was introduced into the sequence using 5 eq. of acid, 5 eq. of HOBT and 5 eq of DIPCDI. 0.53 g of crude product were obtained.

Example 6: Synthesis of Compound 6

```
                                          (SEQ ID NO: 4)
H-L-Ala-Gly-c[L-Cys-L-Lys-L-Asn-L-Phe-L-Dfp-D-Trp-
L-Lys-L-Thr-L-Phe-L-Thr-L-Ser-L-Cys]-OH
```

The compound was prepared using the method described in example 1 and same equivalent ratios. The N-terminal amino acid was added in the form of Boc-Ala-OH. 0.53 g of crude product were obtained.

Characterization: ESI-MS: Theoretical M=1673.9 g/mol, Experimental M: (m/z): [M+H]$^+$=1674.8; [M+2H]$^+$/2=837.9

Example 7: Synthesis of (Ac-SEQ ID NO: 10-NH$_2$) Ac-L-Pro-c[L-Cys-L-Lys-L-Asn-L-Phe-L-Dfp-L-Trp-L-Lys-L-Thr-L-Phe-L-Thr-L-Ser-L-Cys]-L-Lys-NH$_2$ (Compound 7)

The compound was prepared using the method described in example 1, by using MBHA resin and the same equivalent ratios. The N-terminal amino acid was added in the form of Fmoc-Pro-OH. Acetylation was carried out in solid-phase using 5 eq. of acetic anhydride and 10 eq. of DIEA. 0.48 g of crude product were obtained.

Characterization: ESI-MS: Theoretical M=1812.15 g/mol, Experimental M: (m/z): [M+2H]$^+$/2=907.07, [M+3H]$^+$/3=605.05

Example 8: Synthesis of (SEQ ID NO: 13-NH$_2$) H-L-Pro-c[L-Cys-L-Lys-L-Asn-L-Dfp-L-Phe-L-Trp-L-Lys-L-Thr-L-Msa-L-Ser-L-Ser-L-Cys]-L-Lys-NH$_2$ (Compound 8)

The compound was prepared using the method described in example 1, by using MBHA resin and the same equivalent ratios. The N-terminal amino acid was added in the form of Boc-Pro-OH. 0.5 g of crude product was obtained.

Characterization: ESI-MS: Theoretical M=1798.15 g/mol, Experimental M: (m/z): [M+2H]$^+$/2=900.1, [M+3H]$^+$/3=600.3.

Example 9: Synthesis of (SEQ ID NO: 17) H-L-Asp-L-Arg-L-Met-L-Pro-c[L-Cys-L-Arg-L-Asn-L-Msa-L-Phe-L-Trp-L-Lys-L-Thr-L-Phe-L-Thr-L-Ser-L-Cys]-L-Lys-OH (Compound 9)

The compound was prepared using the method described in example 1 and the same equivalent ratios. The N-terminal amino acid was added in the form of Fmoc-Asp(OtBu)-OH. After deprotection of the Fmoc and the final acidolysis, 0.54 g of crude product were obtained.

Characterization: ESI-MS: Theoretical M=2207.54 g/mol, Experimental M: (m/z): [M+2H]$^+$/2=1104.7; [M+3H]$^+$/3=736.8

Example 10: Synthesis of (Myristoyl-SEQ ID NO: 17) Myristoyl-L-Asp-L-Arg-L-Met-L-Pro-c[L-Cys-L-Arg-L-Asn-L-Msa-L-Phe-L-Trp-L-Lys-L-Thr-L-Phe-L-Thr-L-Ser-L-Cys]-L-Lys-OH (Compound 10)

The compound was prepared using the method described in example 1 and the same equivalent ratios. The N-terminal amino acid was added in the form of Fmoc-Asp(OtBu)-OH. The myristic acid was introduced using 5 eq. of acid, 5 eq. of HOBT and 5 eq. of DIPCDI. 0.52 g of crude product were obtained.

Characterization: ESI-MS: Theoretical M=2411.5 g/mol, Experimental M: (m/z): [M+2H]$^+$/2=1206.8; [M+3H]$^+$/3=804.8.

Example 11: Binding Values of the New Cortistatin Analogues to Somatostatin Receptors (Sstr1-Sstr5)

CHO-K1 cells in which each of the 5 somatostatin receptors (sstr1-sstr5) were expressed independently were used. The cells were incubated in HEPES pH7.4 buffer with the new cortistatin analogues (compounds 1-10) at a concentration range from 0.1 nM to 10 μM for 2-4 hours and $^{125}$I-Tyr$^{11}$-somatostatin 14 was used as radioactive ligand and somatostatin-14 as cold ligand. The radioactivity obtained in the absence of somatostatin-14 was considered as the total binding and that obtained in the presence of 1 μM of somatostatin-14 was considered as the non-specific bond. The specific binding was considered as the difference between the complete binding and the non-specific binding. In the concentration range tested from 0.1 nM to 10 μM, the new cortistatin analogues evaluated gave values of percentage of inhibition of specific binding that were higher than 50%. Said values correlated with the IC50 values for the new cortistatin analogues within the following ranges, all of which are in the nanomolar range, (IC50 (sstr1)=1 nM-50 nM; IC50 (sstr2)=1 nM–50 nM; IC50 (sstr3, sstr4 and sstr5)=0.5 nM-5 nM), range of values published for cortistatin [Spier et al., *Brain Research Reviews* 2000, 33, 228-241] IC50 (sstr1)=1-5 nM; IC50 (sstr2, sstr3, sstr5)=0.1 nM–5 nM; IC50 (sstr4)=0.1 nM-20 nM). The results indicate that the new cortistatin analogues evaluated interact with the somatostatin receptors sstr1-sstr with nano-molar affinity.

Example 12. Effect of the New Cortistatin Analogues on Inflammatory Response In Vitro Raw 264 cells were cultured in complete DMEM medium until a confluence of 80% was reached. The cells were incubated either in the absence or presence of lipopolysaccharide (LPS, 1 μg/ml, from *E. coli* serotype 055:B5). The cells incubated in the absence of lipopolysaccharide were used as a reference (basal). The new cortistatin analogues were added at 100 nM concentration at the start of the culture. After 24 hours, the supernatants were collected and cytokine and nitric oxide levels were measured. The cytokine level (TNFalpha and IL-6) was established using a ELISA test. The quantity of nitric oxide (NO) was established using the Griess test. Equal volumes of supernatants from the culture (90 μl) and Griess reagents were mixed and absorbance was measured at 550 nm. The nitrite amount was calculated in relation to a standard NaNO$_2$ curve.

For comparison, the values of cortistatin-14 (CST-14), somatostatin-14 (SOM-14) and three somatostatin analogues described in WO 2010/128098 A1 were evaluated:

```
                                          (SEQ ID NO: 19)
H-L-Ala-Gly-c[L-Cys-L-Lys-L-Asn-L-Msa-L-Phe-L-Trp-
L-Lys-L-Thr-L-Phe-L-Thr-L-Ser-L-Cys]-OH (compound
11)
```

(SEQ ID NO: 20)
H-L-Ala-Gly-c[L-Cys-L-Lys-L-Asn-L-Phe-L-Msa-L-Trp-
L-Lys-L-Thr-L-Phe-L-Thr-L-Ser-L-Cys]-OH (compound
12)

(SEQ ID NO: 21)
H-L-Ala-Gly-c[L-Cys-L-Lys-L-Asn-L-Phe-L-Phe-L-Trp-
L-Lys-L-Thr-L-Msa-LThr-L-Ser-L-Cys]-OH (compound
13)

respectively. The corresponding basal values in the absence of inflammation were 0.48 ng/mL; 0 ng/mL and 0.44 ng/mL. The TNFalpha, IL-6 and NO values obtained after treatment with the native peptide, CST-14, were 3.17 ng/mL; 3.78 ng/mL and 3.08 ng/mL respectively, all of which are below the maximum measurement values of inflammation, therefore CST-14 indicated an anti-inflammatory efficacy. The values obtained for SST-14 were 5.21 ng/mL; 4.2 ng/mL and 4.32 ng/mL, and the values for the studied somatostatin analogues (compounds 11-13) were found in the ranges 5.18-5.24 ng/mL; 4.19-4.45 ng/mL and 3.4-5.05 ng/mL respectively.

The values obtained after treatment with the new cortistatin analogues were found in the ranges 2.51-4.9 ng/mL; 2.77-4.23 ng/mL and 3.04-4.49 ng/mL respectively for TNFalpha, IL-6 and NO, demonstrating the efficacy of said treatments in reducing inflammation in vitro, higher than that of the tested somatostatin analogues (compounds 11-13).

The data obtained for CST-14 and SST-14 indicate that both molecules and their analogues are effective in reducing inflammation in vitro.

Example 13. Effect of the New Cortistatin Analogues on Immune Response In Vitro Splenocytes from 8 week old male C57B1I/6 mice were obtained after mechanical dissociation of cells, filtration through a nylon mesh and lysis of red blood cells. The splenocytes were incubated in complete DMEM medium until a density of $10^6$ cells/ml. The non-adherent cells (formed in 80% by T cells) were used for measuring cytokines and for proliferation assays. The T cells were cultured in complete DMEM medium and stimulated with anti-CD3 antibodies (2 µg/ml) in the presence of different cortistatin analogues at a concentration of 100 nM. After 48 hours, the supernatants of the culture were isolated and the levels of cytokines (IFNγ and IL-2) were determined by using an ELISA test. In order to determine the effect of the different cortistatin analogues in proliferation, the cells were cultured for 72 hours and 0.5 µCi (0.0185 MBq)/well of [$^3$H]— thymidine was added for the last 8 hours of culture, the membranes were collected and the added [$^3$H]-Thymidine was measured using a scintillation counter.

For comparison, the values of cortistatin-14 (CST-14), somatostatin-14 (SOM-14) and three somatostatin analogues described in WO 2010/128098 A1 were determined:

(SEQ ID NO: 19)
H-L-Ala-Gly-c[L-Cys-L-Lys-L-Asn-L-Msa-L-Phe-L-Trp-
L-Lys-L-Thr-L-Phe-L-Thr-L-Ser-L-Cys]-OH (compound
11)

(SEQ ID NO: 20)
H-L-Ala-Gly-c[L-Cys-L-Lys-L-Asn-L-Phe-L-Msa-L-Trp-
L-Lys-L-Thr-L-Phe-L-Thr-L-Ser-L-Cys]-OH (compound
12)

(SEQ ID NO: 21)
H-L-Ala-Gly-c[L-Cys-L-Lys-L-Asn-L-Phe-L-Phe-L-Trp-
L-Lys-L-Thr-L-Msa-LThr-L-Ser-L-Cys]-OH (compound
13)

As the maximum measurement of immune response, the obtained activated values of proliferation, INFγ and IL-2 were 9843; 2.52 ng/mL and 3.22 ng/mL respectively. The corresponding basal values in the absence of activation of an immune response were 640; 0 ng/mL and 0.23 ng/mL. The values of proliferation, INFγ and IL-2 obtained after treatment with the native peptide, CST-14, were 5500; 1.13 ng/mL and 1.52 ng/mL respectively, all of which are below the maximum values of immune response, indicating CST-14's efficacious modulation of immune response. The values obtained for SST-14 were 9936; 2.31 ng/mL and 3.14 ng/mL, and the values of the studied somatostatin analogues (compounds 11-13) were found in the ranges 10216-10466; 2.51-2.3 ng/mL and 3.23-3.37 ng/mL respectively.

The values obtained after treatment with the new cortistatin analogues were found in the ranges 5863-9316; 1.33-2.56 ng/mL and 1.8-3.23 ng/mL respectively for proliferation, INFγ and IL-2, demonstrating the efficacy of said treatments in reducing immune response in vitro.

Treatment of the activated splenocytes with the new cortistatin analogues reduced the levels of proliferation, INFγ and/or IL-2, indicating effectiveness in the modulation of the over-activation of immune response.

The comparative data obtained for CST-14 and its new analogues and SST-14 and its analogues indicate that CST-14 and analogues have a greater effect in reducing immune response in vitro.

Example 14: Serum Stability of the New Cortistatin Analogues

The new compounds were incubated with 90% human serum at 37° C. Aliquots were extracted at different incubation times. Methanol was added to precipitate the proteins from the serum, it was centrifuged and the supernatant was subject to a chromatographic analysis using RP-HPLC (Gradient: 20-80% B in 30 min, B=0.07% TFA in acetonitrile). The disappearance of the initial product was analyzed using the area corresponding to the initial product and half-life time was calculated.

The new compounds have a half-life that is longer than that of cortistatin. In these experimental conditions, the half-life of cortistatin in serum was 2 minutes. The half-life of compounds 4, 6 and 5 is 21 minutes, 3.8 hours and 35 hours respectively. For CST-14, the main metabolite is compound 14. The main metabolite of compound 4 is compound 5. In both cases, the initial peptide loses Lys on the C-terminal resulting in a metabolite that is stable for hours.

(SEQ ID NO: 22)
H-Pro-c[Cys-Lys-Asn-Phe-Phe-Trp-Lys-Thr-Phe-Ser-Ser-Cys]-OH (compound 14)

Example 15: Efficacy of Compounds 4, 5 and 6 in a Model of Collagen Induced Arthritis (CIA) in Mice DBA/1 mice were injected with type II chicken collagen in complete Freud's adjuvant and *M. tuberculosis* on days 0 and 21. Between days 25 and 29 the mice were subcutaneously treated with saline (control) or with 0.4 mg/kg of compounds 4, 5 or 6 once a day. As a reference treatment, an anti-TNFalpha antibody was used and was injected intravenously on days 25 and 32. The clinical grade of arthritis was analysed daily using numbers from 0 to 10 in accordance with the severity of the damage. Paw swelling was assessed by measuring thickness with a calliper every five days throughout the study (days 20, 25, 30, 35, 40, 45, 50).

Treatment of the CIA mice with compounds 4, 5 and 6 shows a substantial improvement in reducing the clinical grade of arthritis and lessening paw swelling, indicating its efficacy in this experimental model of an illness with inflammatory and immune response. The clinical grade of arthritis (0-10) of the ill mice treated with saline (control) reached a maximum value of 8.5 on day 21 after the second collagen injection. In the same period, treatment of those CIA mice with the compounds of this invention (compounds 4-6) reduced the grade of arthritis to values within a range from 3 to 5.6. It is worth pointing out that these values are within the range that includes the value of the grade of arthritis obtained for CIA mice treated with an anti-TNF alpha positive control (4.9) equivalent to clinically used treatments for rheumatoid arthritis.

On day 50 of the study, the thickness of the sick CIA mice's paws reached a value of 2.83 mm. The anti-TNFalpha control reduced inflammation in the paws to a value of 2.5 mm. Compounds 4-6 also reduced inflammation values to between 2.3-2.5 mm.

Example 16: Efficacy of Compounds 4, 5 and 6 in an Experimental Model of Crohn's Disease 6-8 week old BALB/c male mice were used. They were intrarectally administered with trinitrobenzenesuphonic acid (TBNS) in 50% of ethanol in order to induce colitis. The control mice received 50% ethanol. The mice were treated subcutaneously with a buffer (PBS) or with different cortistatin analogues (0.4 mg/Kg) on days 3, 4 and 5, when the disease was already established.

The animals were observed daily and the presence of diarrhea (grade of colitis) by using a scale of 0 to 4, weight loss and survival were monitored. Furthermore, at necropsy, in the day 10, the colons were evaluated and classified according to macroscopic damage using a scale from 0 to 10 based on criteria that reflected inflammation, hyperaemia, swelling of the colon, and extension of the ulceration by two independent researchers in blinded manner. The classification of the grade of colitis, according to stool consistency and rectal bleeding, was also carried out by two independent observers: 0=normal stool appearance, 1=slight decrease in stool consistency; 2=moderate decrease in stool consistency; 3=moderate decrease in stool consistency and presence of blood in stools; 4=severe watery diarrhea and moderate/severe blooding in stools. The weight of the mice suffering from colitis induced by TNBS treatment in 50% ethanol dropped from day 1 (22 g) to day 10 (17 g). The weight of the healthy control mice only treated with 50% ethanol increased from day 1 (22 g) to day 10 (25 g). The treatment of sick mice with the anti-TNFalpha positive control moderated their weight loss from day 1 (21 g) to day 10 (19 g); the same occurred with treatment with cortistatin analogue compounds 4-6, in which their weight on day was between 19 and 20 g, values that are significantly higher than the weight value obtained for sick mice (17 g).

The grade of colitis (0-4) evaluated in vivo on day 6 of the study showed a basal value of 0.25 for healthy control mice treated with 50% ethanol and a maximum value of 3.6 for the sick mice treated with TBNS in 50% ethanol. The different treatments with cortistatin analogues resulted in grade of colitis values between 1.4 and 2.1, similar to that of the positive control group treated with anti-TNFalpha (2.1), indicating the efficacy of said treatments.

The extent of macroscopic damage in the colon (0-10) was analysed in the necropsy. A basal value of 0.2 was obtained for the healthy control mice treated with 50% ethanol and a maximum value of 7.5 for the sick mice treated with TBNS in 50% ethanol. The different treatments with the cortistatin analogues showed values of the extent of damage between 1.9 and 2.8. Treatment with the anti-TNFalpha compound gave a value of 2.5 in the same range as those compounds of this invention.

Example 17: Efficacy of Compounds 4, 5 and 6 in an Experimental Model of Ulcerative Colitis 7-8 week old $C_{57}Bl/6$ male mice were used. They were given voluntary drinking water with 5% of Dextran sulfate sodium (DSS) from day 0 to day 7 of the study in order to induce acute colitis. Animals in the control group were supplied with normal water. The mice were treated subcutaneously with (PBS) buffer or with the different cortistatin analogues (0.4 mg/Kg) on days 1, 2 and 3 of the study. CST was used as a reference product. The severity of the colitis was assessed daily using a scale of values from 0 to 4 indicating the clinical disease activity index considering stool consistency, the presence of bloody stools and weight loss. Mice were sacrificed on day 8 of the study and after the necropsy the extent of macroscopic damage was established in the colon using a scale from 0 to 8. Oral administration of 5% DSS resulted in a significant increase in the disease activity index (0-4), going from a basal value of 0 to a value of 3.7 in the diseased group. The sick mice treated with CST and cortistatin analogues obtained clinical disease activity index values significantly lower and similar therein, in the range of 1-1.5. Furthermore, treatment with the new cortistatin analogues between days 1 and 3 of the study significantly increased survival of the sick animals from 50% to 100%. On a macroscopic level, the grade of colitis of the sick mice was 6.6; that of those sick mice treated with CST was 0.87 and that of the sick mice treated with the new cortistatin analogues was 0.74-1.5. The average weight of the sick mice's colons was 763 mg, the average weight of the colons of the sick mice treated with CST was 621 mg and that of the colons of the sick mice treated with the new cortistatin analogues was between 614-621 mg, indicating a reduction of the inflammation of the colon. All these results demonstrate the efficacy, in this experimental model of colitis, of the new cortistatin analogues.

The invention claimed is:

1. A cortistatin analogue compound selected from the group consisting of:

(SEQ ID NO: 4)
H-L-Ala-Gly-c[L-Cys-L-Lys-L-Asn-L-Phe-L-Dfp-D-Trp-L-Lys-L-Thr-L-Phe-L-Thr-L-Ser-L-Cys]-OH, (Octanoyl-SEQ ID NO: 8)
Octanoyl-L-Pro-c[L-Cys-L-Lys-L-Asn-L-Msa-L-Phe-D-Trp-L-Lys-L-Thr-L-Phe-L-Thr-L-Ser-L-Cys]-L-Lys-OH, (Octanoyl-SEQ ID NO: 14)
Octanoyl-L-Pro-c[L-Cys-L-Lys-L-Asn-L-Msa-L-Phe-D-Trp-L-Lys-L-Thr-L-Phe-L-Thr-L-Ser-L-Cys]-OH, its stereoisomers, mixtures thereof or its pharmaceutically acceptable salts thereof, and wherein the compound has cortistatin anti-inflammatory and immunoregulatory activity.

2. A process for the preparation of a compound as defined in claim 1, its stereoisomers, mixtures thereof, or its pharmaceutically acceptable salts, which is carried out using solid phase synthesis or synthesis in solution.

3. The process according to claim 2, comprising:
 1. Solid phase synthesis
 2. Cleavage of the peptide from the polymeric support
 3. Cyclization of the peptide in solution
 4. Removal of the protecting groups or alternatively,
 1. Solid phase synthesis
 2. Solid phase cyclization
 3. Cleavage of the peptide from the polymeric support and simultaneous removal of the protecting groups, preferably via treatment with trifluoroacetic acid.

4. A pharmaceutical composition which comprises a pharmaceutically effective amount of at least one compound according to claim 1, its stereoisomers, mixtures thereof, or its pharmaceutically acceptable salts.

5. The pharmaceutical composition according to claim 4, wherein the compound, its stereoisomers, mixtures thereof or its pharmaceutically acceptable salts is incorporated into a delivery system and/or a pharmaceutical sustained release system selected from the group consisting of liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules, nanocapsules, microemulsions and nanoemulsions.

6. The pharmaceutical composition according to claim 4, wherein the composition further comprises at least one therapeutic agent selected from the group consisting of other anti-inflammatory agents, immunosuppressive agents, metabolic and enzyme inhibitors, non-steroidal anti-inflammatory agents, ibuprofen, tenidap, naproxen, meloxicam, mesalazine, piroxicam, diclofenac, indomethacin, sulfasalazine, corticosteroids, prednisolone, hydrocortisone, beclomethasone, budesonide, cytokine-suppressant anti-inflammatory drugs, nucleotide synthesis inhibitors, methotrexate, leflunomide, immunosuppressors, cyclosporin, tacrolimus, mTOR inhibitors, sirolimus or rapamycin and derivatives thereof, tumor necrosis factor TNFα inhibiting agents, infliximab, adalimumab, etanercept, certolizumab, golimumab, COX-2 inhibitors, celecoxib, rofecoxib, valdecoxib and variants thereof, phosphodiesterase inhibitors, phospholipase inhibitors, trifluoromethyl ketone analogues, vascular endothelial growth factor inhibitors, growth factor receptor inhibitors, angiogenesis inhibitors, natalizumab, rituximab, abatacept, fostamatinib, tocilizumab, anakinra, tofacitinib, 6-mercaptopurines, azathioprine, balsalazide, sulfasalazine, mesalazine, olsalazine, chloroquine, hydroxychloroquine, penicillamine, auranofin, aurothiomalate, azathioprine, colchicine, beta-2 adrenergic receptor agonists, salbutamol, terbutaline and salmeterol, xanthines, theophylline, arninophylline, cromoglycate, nedocromil, ketotifen, ipratropium, oxitropium, mycophenolate mofetil, adenosine agonists, anti-thrombosis agents, penicillin, complement inhibitors and adrenergic agents.

7. The pharmaceutical composition according to claim 4, which is administered by topical, enteral or parenteral routes.

* * * * *

SEQUENCE LISTING

<160> NUMBER OF SEQ ID NOS: 22

<210> SEQ ID NO 1
<211> LENGTH: 14
<212> TYPE: PRT
<213> ORGANISM: Unknown
<220> FEATURE:
<223> OTHER INFORMATION: Cortistatin-14 (mouse/rat)
<220> FEATURE:
<221> NAME/KEY: DISULFID
<222> LOCATION: (2)..(13)

<400> SEQUENCE: 1

Pro Cys Lys Asn Phe Phe Trp Lys Thr Phe Ser Ser Cys Lys
1               5                   10

<210> SEQ ID NO 2
<211> LENGTH: 17
<212> TYPE: PRT
<213> ORGANISM: Unknown
<220> FEATURE:
<223> OTHER INFORMATION: Cortistatin-17 (Homo sapiens)
<220> FEATURE:
<221> NAME/KEY: DISULFID
<222> LOCATION: (5)..(16)

<400> SEQUENCE: 2

Asp Arg Met Pro Cys Arg Asn Phe Phe Trp Lys Thr Phe Ser Ser Cys
1               5                   10                  15

Lys

<210> SEQ ID NO 3
<211> LENGTH: 14
<212> TYPE: PRT
<213> ORGANISM: Unknown
<220> FEATURE:
<223> OTHER INFORMATION: Somatostatin-14
<220> FEATURE:
<221> NAME/KEY: DISULFID
<222> LOCATION: (3)..(14)

<400> SEQUENCE: 3

Ala Gly Cys Lys Asn Phe Phe Trp Lys Thr Phe Thr Ser Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (3)..(14)
<220> FEATURE:
<221> NAME/KEY: VARIANT
<222> LOCATION: (7)..(7)
<223> OTHER INFORMATION: Xaa= 3,5-difluorophenylalanine

<400> SEQUENCE: 4

Ala Gly Cys Lys Asn Phe Xaa Trp Lys Thr Phe Thr Ser Cys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide

```
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: Xaa= 3,5-difluorophenylalanine

<400> SEQUENCE: 5

Ala Gly Cys Lys Asn Xaa Phe Trp Lys Thr Phe Thr Ser Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (3)..(14)
<220> FEATURE:
<221> NAME/KEY: VARIANT
<222> LOCATION: (11)..(11)
<223> OTHER INFORMATION: Xaa= 3,5-difluorophenylalanine

<400> SEQUENCE: 6

Ala Gly Cys Lys Asn Phe Phe Trp Lys Thr Xaa Thr Ser Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: Xaa= 3,5-difluorophenylalanine
<220> FEATURE:
<221> NAME/KEY: VARIANT
<222> LOCATION: (11)..(11)
<223> OTHER INFORMATION: Xaa= 3,5-difluorophenylalanine

<400> SEQUENCE: 7

Ala Gly Cys Arg Asn Xaa Phe Trp Lys Thr Xaa Ser Ser Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(13)
<220> FEATURE:
<221> NAME/KEY: VARIANT
<222> LOCATION: (5)..(5)
<223> OTHER INFORMATION: Xaa= 2,4,6-trimethylphenylalanine

<400> SEQUENCE: 8

Pro Cys Lys Asn Xaa Phe Trp Lys Thr Phe Thr Ser Cys Lys
1               5                   10

<210> SEQ ID NO 9
```

```
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(13)
<220> FEATURE:
<221> NAME/KEY: VARIANT
<222> LOCATION: (6)..(6)
<223> OTHER INFORMATION: Xaa= 2,4,6-trimethylphenylalanine

<400> SEQUENCE: 9

Pro Cys Lys Asn Phe Xaa Trp Lys Thr Phe Thr Ser Cys Lys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(13)
<220> FEATURE:
<221> NAME/KEY: VARIANT
<222> LOCATION: (6)..(6)
<223> OTHER INFORMATION: Xaa= 3,5-difluorophenylalanine

<400> SEQUENCE: 10

Pro Cys Lys Asn Phe Xaa Trp Lys Thr Phe Thr Ser Cys Lys
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(13)
<220> FEATURE:
<221> NAME/KEY: VARIANT
<222> LOCATION: (10)..(10)
<223> OTHER INFORMATION: Xaa= 2,4,6-trimethylphenylalanine

<400> SEQUENCE: 11

Pro Cys Lys Asn Phe Phe Trp Lys Thr Xaa Thr Ser Cys Lys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(13)
<220> FEATURE:
<221> NAME/KEY: VARIANT
<222> LOCATION: (5)..(5)
<223> OTHER INFORMATION: Xaa= 2,4,6-trimethylphenylalanine
<220> FEATURE:
<221> NAME/KEY: VARIANT
<222> LOCATION: (10)..(10)
<223> OTHER INFORMATION: Xaa= 2,4,6-trimethylphenylalanine

<400> SEQUENCE: 12
```

Pro Cys Arg Asn Xaa Phe Trp Lys Thr Xaa Thr Ser Cys Lys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(13)
<220> FEATURE:
<221> NAME/KEY: VARIANT
<222> LOCATION: (5)..(5)
<223> OTHER INFORMATION: Xaa= 3,5-difluorophenylalanine
<220> FEATURE:
<221> NAME/KEY: VARIANT
<222> LOCATION: (10)..(10)
<223> OTHER INFORMATION: Xaa= 2,4,6-trimethylphenylalanine

<400> SEQUENCE: 13

Pro Cys Lys Asn Xaa Phe Trp Lys Thr Xaa Ser Ser Cys Lys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(13)
<220> FEATURE:
<221> NAME/KEY: VARIANT
<222> LOCATION: (5)..(5)
<223> OTHER INFORMATION: Xaa= 2,4,6-trimethylphenylalanine

<400> SEQUENCE: 14

Pro Cys Lys Asn Xaa Phe Trp Lys Thr Phe Thr Ser Cys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (2)..(13)
<220> FEATURE:
<221> NAME/KEY: VARIANT
<222> LOCATION: (10)..(10)
<223> OTHER INFORMATION: Xaa= 3,5-difluorophenylalanine

<400> SEQUENCE: 15

Pro Cys Lys Asn Phe Phe Trp Lys Thr Xaa Thr Ser Cys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (3)..(14)
<220> FEATURE:
<221> NAME/KEY: VARIANT

```
<222> LOCATION: (6)..(6)
<223> OTHER INFORMATION: Xaa= 2,4,6-trimethylphenylalanine

<400> SEQUENCE: 16

Met Pro Cys Arg Asn Xaa Phe Trp Lys Thr Phe Ser Ser Cys Lys
1               5                   10                  15

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (5)..(16)
<220> FEATURE:
<221> NAME/KEY: VARIANT
<222> LOCATION: (8)..(8)
<223> OTHER INFORMATION: Xaa= 2,4,6-trimethylphenylalanine

<400> SEQUENCE: 17

Asp Arg Met Pro Cys Arg Asn Xaa Phe Trp Lys Thr Phe Thr Ser Cys
1               5                   10                  15

Lys

<210> SEQ ID NO 18
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (5)..(16)
<220> FEATURE:
<221> NAME/KEY: VARIANT
<222> LOCATION: (8)..(8)
<223> OTHER INFORMATION: Xaa= 3,5-difluorophenylalanine

<400> SEQUENCE: 18

Asp Arg Met Pro Cys Arg Asn Xaa Phe Trp Lys Thr Phe Thr Ser Cys
1               5                   10                  15

Lys

<210> SEQ ID NO 19
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: Xaa= 2,4,6-trimethylphenylalanine

<400> SEQUENCE: 19

Ala Gly Cys Lys Asn Xaa Phe Trp Lys Thr Phe Thr Ser Cys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: DISULFID
<222> LOCATION: (3)..(14)
<220> FEATURE:
<221> NAME/KEY: VARIANT
<222> LOCATION: (7)..(7)
<223> OTHER INFORMATION: Xaa= 2,4,6-trimethylphenylalanine

<400> SEQUENCE: 20

Ala Gly Cys Lys Asn Phe Xaa Trp Lys Thr Phe Thr Ser Cys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (3)..(14)
<220> FEATURE:
<221> NAME/KEY: VARIANT
<222> LOCATION: (11)..(11)
<223> OTHER INFORMATION: Xaa= 2,4,6-trimethylphenylalanine

<400> SEQUENCE: 21

Ala Gly Cys Lys Asn Phe Phe Trp Lys Thr Xaa Thr Ser Cys
1               5                   10

<210> SEQ ID NO 22
<211> LENGTH: 13
<212> TYPE: PRT
<213> ORGANISM: Unknown
<220> FEATURE:
<223> OTHER INFORMATION: Metabolite of cortistatin-14
<220> FEATURE:
<221> NAME/KEY: DISULFID
<222> LOCATION: (2)..(13)

<400> SEQUENCE: 22

Pro Cys Lys Asn Phe Phe Trp Lys Thr Phe Ser Ser Cys
1               5                   10
```